(12) United States Patent
Johnson et al.

(10) Patent No.: US 7,234,225 B2
(45) Date of Patent: Jun. 26, 2007

(54) METHOD FOR MANUFACTURING MEDICAL DEVICE HAVING EMBEDDED TRACES AND FORMED ELECTRODES

(75) Inventors: Michael Johnson, Minneapolis, MN (US); Kirk S. Honour, Minnetonka, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 375 days.

(21) Appl. No.: 10/668,831

(22) Filed: Sep. 22, 2003

(65) Prior Publication Data

US 2005/0060885 A1 Mar. 24, 2005

(51) Int. Cl.
*G01R 31/28* (2006.01)

(52) U.S. Cl. .................... 29/593; 29/825; 29/401.1; 600/374; 607/116; 604/524

(58) Field of Classification Search ................. 29/825, 29/829, 830, 846, 592.1, 594, 25.35; 600/374; 606/41; 607/122; 310/333–336; 264/135, 264/264
See application file for complete search history.

(56) References Cited

U.S. PATENT DOCUMENTS

| | | |
|---|---|---|
| 3,867,945 A | 2/1975 | Long |
| 4,033,331 A | 7/1977 | Guss et al. |
| 4,117,836 A | 10/1978 | Erikson |
| 4,244,362 A | 1/1981 | Anderson |
| 4,445,892 A | 5/1984 | Hussein et al. |
| 4,500,529 A | 2/1985 | Shanklin, Jr. et al. |
| 4,558,155 A | 12/1985 | Shanklin, Jr. et al. |
| 4,569,347 A | 2/1986 | Frisbie |
| 4,581,017 A | 4/1986 | Sahota |
| 4,641,649 A | 2/1987 | Walinsky et al. |
| 4,705,517 A | 11/1987 | DiPisa, Jr. |
| 4,721,117 A | 1/1988 | Mar et al. |
| 4,729,384 A | 3/1988 | Bazenet |
| 4,790,331 A | 12/1988 | Okeda et al. |
| 4,810,244 A | 3/1989 | Allen |

(Continued)

FOREIGN PATENT DOCUMENTS

DE 40 01 086 7/1991

(Continued)

OTHER PUBLICATIONS

Cox, J. L. et al., Electrophysiology, Pacing and Arrhythmia, "Operations for Atrial Fibrillation", Clin. Cardiol. vol. 14, pp. 827-834 (1991).

(Continued)

Primary Examiner—Minh Trinh
(74) Attorney, Agent, or Firm—Heimbecher & Assoc., LLC

(57) ABSTRACT

Disclosed is a method of manufacturing a catheter or lead having electrically conductive traces and external electrical contacts. Each trace may be in electrical connection with one or more external electrical contacts. More specifically, each trace is typically electrically connected to a single contact. The traces and contacts may assist in diagnosis and/or detection of bio-electric signals emitted by organs, and may transmit such signals to a connector or diagnostic device affixed to the catheter. The external contacts may detect bioelectric energy or may deliver electrical energy to a target site.

18 Claims, 20 Drawing Sheets

U.S. PATENT DOCUMENTS

| | | | |
|---|---|---|---|
| 4,838,879 A | 6/1989 | Tanabe et al. | |
| 4,867,174 A | 9/1989 | Skribiski | |
| 4,882,777 A | 11/1989 | Narula | |
| 4,883,058 A | 11/1989 | Ruiz | |
| 4,898,591 A | 2/1990 | Jang et al. | |
| 4,911,163 A | 3/1990 | Fina | |
| 4,917,102 A | 4/1990 | Miller et al. | |
| 4,935,017 A | 6/1990 | Sylvanowicz | |
| 4,945,912 A | 8/1990 | Langberg | |
| 4,955,377 A | 9/1990 | Lennox et al. | |
| 4,969,875 A | 11/1990 | Ichikawa | |
| 4,988,698 A | 1/1991 | Kato et al. | |
| 5,002,532 A | 3/1991 | Gaiser et al. | |
| 5,016,640 A | 5/1991 | Ruiz | |
| 5,052,407 A | 10/1991 | Hauser et al. | |
| 5,100,388 A | 3/1992 | Behl et al. | |
| 5,103,804 A | 4/1992 | Abele et al. | |
| 5,106,360 A | 4/1992 | Ishiwara et al. | |
| 5,120,323 A | 6/1992 | Shockey et al. | |
| 5,147,315 A | 9/1992 | Weber | |
| 5,162,911 A | 11/1992 | Burrage | |
| 5,171,232 A | 12/1992 | Castillo et al. | |
| 5,172,699 A | 12/1992 | Svenson et al. | |
| 5,209,229 A | 5/1993 | Gilli | |
| 5,215,540 A | 6/1993 | Anderhub | |
| 5,215,989 A | 6/1993 | Baldwin et al. | |
| 5,222,501 A | 6/1993 | Ideker et al. | |
| 5,228,442 A | 7/1993 | Imran | |
| 5,231,994 A | 8/1993 | Harmjanz | |
| 5,231,995 A | 8/1993 | Desai | |
| 5,242,441 A | 9/1993 | Avitall | |
| 5,246,007 A | 9/1993 | Frisbie et al. | |
| 5,246,438 A | 9/1993 | Langberg | |
| 5,256,141 A | 10/1993 | Gencheff et al. | |
| 5,263,493 A | 11/1993 | Avitall | |
| 5,267,982 A | 12/1993 | Sylvanowicz | |
| 5,271,392 A | 12/1993 | Ferek-Petric | |
| 5,279,546 A | 1/1994 | Mische et al. | |
| 5,281,213 A | 1/1994 | Milder et al. | |
| 5,281,217 A | 1/1994 | Edwards et al. | |
| 5,281,218 A | 1/1994 | Imran | |
| 5,282,836 A | 2/1994 | Kreyenhagen et al. | |
| 5,286,866 A | 2/1994 | Carr et al. | |
| 5,287,858 A | 2/1994 | Hammerslag et al. | |
| 5,290,229 A | 3/1994 | Paskar | |
| 5,293,868 A | 3/1994 | Nardella | |
| 5,295,493 A | 3/1994 | Radisch, Jr. | |
| 5,299,574 A | 4/1994 | Bower | |
| 5,304,131 A | 4/1994 | Paskar | |
| 5,304,214 A | 4/1994 | DeFord et al. | |
| 5,312,355 A | 5/1994 | Lee | |
| 5,322,509 A | 6/1994 | Rickerd | |
| 5,359,760 A * | 11/1994 | Busse et al. | 29/25.35 |
| 5,366,490 A | 11/1994 | Edwards et al. | |
| 5,417,208 A | 5/1995 | Winkler | |
| 5,427,119 A | 6/1995 | Swartz et al. | |
| 5,433,729 A | 7/1995 | Adams et al. | |
| 5,450,846 A | 9/1995 | Goldreyer | |
| 5,462,529 A | 10/1995 | Simpson et al. | |
| 5,468,239 A | 11/1995 | Tanner et al. | |
| 5,472,441 A | 12/1995 | Edwards et al. | |
| 5,476,495 A | 12/1995 | Kordis et al. | |
| 5,484,412 A | 1/1996 | Pierpont | |
| 5,497,774 A | 3/1996 | Swartz et al. | |
| 5,536,247 A | 7/1996 | Thornton | |
| 5,540,679 A | 7/1996 | Fram et al. | |
| 5,564,440 A | 10/1996 | Swartz et al. | |
| 5,575,766 A | 11/1996 | Swartz et al. | |
| 5,584,872 A | 12/1996 | LaFontaine et al. | |
| 5,588,961 A | 12/1996 | Leone et al. | |
| 5,599,307 A | 2/1997 | Bacher et al. | |
| 5,624,439 A | 4/1997 | Edwards et al. | |
| 5,628,316 A | 5/1997 | Swartz et al. | |
| 5,640,955 A | 6/1997 | Ockuly et al. | |
| 5,676,693 A | 10/1997 | LaFontaine | |
| 5,681,308 A | 10/1997 | Edwards et al. | |
| 5,722,400 A | 3/1998 | Ockuly et al. | |
| 5,746,495 A | 5/1998 | Klamm | |
| 5,779,644 A * | 7/1998 | Eberle et al. | 600/463 |
| 5,785,706 A | 7/1998 | Bednarek | |
| 5,792,105 A | 8/1998 | Lin et al. | |
| 5,797,905 A | 8/1998 | Fleischman et al. | |
| 5,800,482 A | 9/1998 | Pomeranz et al. | |
| 5,803,083 A * | 9/1998 | Buck et al. | 600/439 |
| 5,807,306 A | 9/1998 | Shapland et al. | |
| 5,814,029 A | 9/1998 | Hassett | |
| 5,824,026 A | 10/1998 | Diaz | |
| 5,938,660 A | 8/1999 | Swartz et al. | |
| 5,971,983 A | 10/1999 | Lesh | |
| 6,068,629 A | 5/2000 | Haissaguerre et al. | |
| 6,097,976 A | 8/2000 | Yang et al. | |
| 6,120,500 A | 9/2000 | Bednarek et al. | |
| 6,156,018 A | 12/2000 | Hassett | |
| 6,235,025 B1 | 5/2001 | Swartz et al. | |
| 6,251,109 B1 | 6/2001 | Hassett et al. | |
| 6,360,128 B2 | 3/2002 | Kordis et al. | |
| 6,503,247 B2 | 1/2003 | Swartz et al. | |
| 6,526,302 B2 | 2/2003 | Hassett | |
| 6,540,744 B2 | 4/2003 | Hassett et al. | |
| 6,976,986 B2 * | 12/2005 | Berube | 606/33 |
| 2005/0060885 A1 * | 3/2005 | Johnson et al. | 29/846 |
| 2005/0065508 A1 * | 3/2005 | Johnson et al. | 606/41 |

FOREIGN PATENT DOCUMENTS

| | | |
|---|---|---|
| EP | A 656217 | 6/1995 |
| EP | A 670168 | 9/1995 |
| WO | WO 92/12754 | 8/1992 |
| WO | WO 92/19307 | 11/1992 |
| WO | WO 96/00042 | 1/1996 |
| WO | WO 97/16127 | 5/1997 |

OTHER PUBLICATIONS

Cox, J. L. et al., "The Surgical Treatment of Atrial Fibrillation", The Journal of Thoracic and Cardiovascular Surgery, vol. 101, No. 4, pp. 569-592 (Apr. 1991).

Cox, J. L. et al., "The Surgical Treatment of Atrial Fibrillation", The Journal of Thoracic and Cardiovascular Surgery, vol. 101, No. 4, pp. 406-426 (Mar. 1991).

Falk, R. H. et al., Atrial Fibrillation Mechanisms and Management, pp. 359-374 (1992).

Heinz, G. et al., "Improvement in Left Ventricular Systolic Function After Successful Radiofrequency His Bundle Ablation for Drug Refractory, Chronic Atrial Fibrillation and Recurrent Atrial Flutter", Am. J. Cordiol., vol. 69, pp. 489-492 (Feb. 15, 1992).

Huang, S. K. et al., "Closed Chest Catheter Desiccation of the Atrioventricular Junction Using Radiofrequency Energy—A New Method of Catheter Ablation", J. Am. Coll. Cardiol., vol. 9, No. 2, pp. 349-358 (Feb. 1987).

Horowitz, L. N., Current Management of Arrhythmias, pp. 373-378 (1991).

Gallagher, J. J. et al., Catheter Technique for Closed-Chest Ablation of the Atrioventricular Conduction System, N. Engl. J. Med., vol. 306, pp. 194-200 (Jan. 28, 1982).

Martin, D. et al., "Artial Fibrillation", pp. 35-59 (1994).

Saul, J. P. et al., "Catheter Ablation of Accessory Atrioventricular Pathways in Young Patients: Use of Long Vascular Sheaths, the Transseptal Approach and a Retrograde Left Posterior Parallel Approach", J. Amer. Coll. Card., vol. 21, No. 3, pp. 571-583 (Mar. 1, 1993).

Scheinman, M. M. et al., "Catheter-Induced Ablation of the Artioventricular Junction to Control Refractory Supraventricular Arrhythmias", JAMA, vol. 248, pp. 851-855 (Aug. 20, 1982).

Swartz, J. F. et al., "Radiofrequency Endocardial Catheter Ablation of Accessory Atrioventricular Pathway Atrial Insertion Sites", Circulation, vol. 87, No. 2, pp. 487-499 (Feb. 1993).

Singer, I. et al., "Catheter Ablation for Arrhythmias", Clinical Manual of Electrophysiology, pp. 421-431 (1993).

Tracy, C. M., "Radiofrequency Catheter Ablation of Ectopic Atrial Tachycardia Using Paced Activation Sequence Mapping", J. Am. Coll. Cardiol., vol. 21, pp. 910-917 (Mar. 15, 1993).

Haissaguerre, M. et al., "Right and Left Atrial Radiofrequency Catheter Therapy of Paroxysmal Atrial Fibrillation", Journal of Cardiovascular Electrophysiology, vol. 7, No. 12, pp. 1132-1144 (Dec. 1996).

* cited by examiner

METHOD FOR MANUFACTURING MEDICAL DEVICE HAVING EMBEDDED TRACES AND FORMED ELECTRODES

This application is related to U.S. patent application Ser. No. 10/668,843, filed Sep. 22, 2003, entitled "Medical Device Having Integral Traces and Formed Electrodes."

FIELD OF THE INVENTION

The invention relates generally to the field of medical instruments, and more particularly to a medical instrument for introduction into a body and having arbitrarily-shaped electrically conductive surfaces formed thereon.

BACKGROUND ART

Catheters have been in use for medical procedures for many years. Among other uses, catheters can be used for medical procedures to examine, diagnose, and/or treat tissue while positioned at a specific location within the body otherwise inaccessible without more invasive procedures. For example, one procedure (often referred to as "catheter ablation") utilizes a catheter to convey electrical energy to a selected location within the human heart to necrotize cardiac tissue. This procedure is often colloquially referred to as "ablation" of cardiac tissue.

Another procedure, oftentimes referred to as "mapping," utilizes a catheter with sensing electrodes to monitor various forms of electrical activity in the human body. Various organs, including the heart and brain, may be mapped by a catheter having appropriate diagnostic functions. Mapping may be thought of as the opposite of ablation, in some respects. Specifically, a mapping catheter detects bioelectric impulses generated by the tissue in question and relays these bioelectric impulses to a diagnostic machine operably attached to the catheter. Accordingly, instead of transmitting energy to tissue, the mapping catheter transmits energy from tissue.

Regardless of the direction of energy transmission, present catheters generally mechanically mount the energy delivery media, such as electrodes, to the catheter surface. Further, the transmission media, typically one or more wires, is generally strung through an opening in the center of the catheter, and is not attached to the catheter save at the connection point with the energy delivery medium. Accordingly, as the catheter is steered, bent, or moved, stress may be applied to the internal wires. Additionally, when medical instruments are inserted into the catheter interior, the surgeon must exercise some degree of care to ensure the instruments do not interfere with the diagnostic functions of the catheter or, possibly, damage the wires.

Further, many diagnostic and energy delivery catheters have multiple wires running to a variety of diagnostic or energy delivery sites. At the catheter's proximal end, these wires often simply terminate with little or no identification separating one wire from the next, making attaching a wire to the appropriate connector pin of a medical device difficult.

Apparatus leads often suffer from similar problems. Leads may be used to deliver energy to tissue, typically in order to regulate tissue contraction through timed pulses of electricity. Such regulation may occur, for example, by a pacemaker. Further, in many neurosurgical applications, leads or catheters may be used to map an area of the brain by electrical measurement, as described above, or by electrically stimulating a portion of the brain to elicit a response. Energy may be further delivered through a lead to ablate tissue and alleviate irregular symptoms plaguing the tissue. In any of these energy-delivery applications, however, the problems identified above typically still exist.

Accordingly, there is a need for an improved medical device capable of transmitting electrical energy across its length either to or from a target site.

SUMMARY OF INVENTION

Generally, one embodiment of the present invention takes the form of a catheter having electrically conductive traces and external electrical contacts. Each trace may be in electrical connection with one or more external electrical contacts. More specifically, each trace is typically electrically connected to a single contact. The traces and contacts may assist in diagnosis and/or detection of bio-electrical signals emitted by organs, and may transmit such signals to a connector or diagnostic device affixed to the catheter.

In another embodiment, a catheter may be provided with energy-conductive traces or wires and external energy emission sites capable of delivering electrical or thermal energy to a target site within or on a patient's body. The conductive wires may be braided, channeled, run through, or formed within the catheter's wall structure. The wires are generally flexible and permit bending and movement of the catheter as necessary. Where electrical energy is channeled through the wires or traces, electrodes are generally formed on the outside of the catheter. If a significant quantity of energy must be delivered, multiple traces may be connected to a single electrode, or wires may be used in lieu of a single trace.

Yet another embodiment takes the form of a lead having integrated, electrically-conductive traces and electrodes formed along its exterior. The distal portion of the lead may be placed within a patient's body and the proximal end connected to a pacemaker or other medical device. The traces and electrodes facilitate monitoring the patient's condition and, if appropriate for the attached device, regulating tissue contraction by delivering timed pulses of electrical energy along the trace, through the electrode, and to the tissue. Where a significant quantity of energy must be delivered, multiple traces or wires may be used in lieu of a single trace.

In yet another embodiment of the present invention, a medical device may be provided with one or more arbitrarily-shaped electrodes on its surface, for example at the device tip. These arbitrarily-shaped electrodes operate in either a diagnostic or energy-delivering mode, as necessary. The arbitrarily-shaped electrodes may obtain improved information on electrical signal directional propagation when recording tissue responses to electrical energy, and may also improve accuracy when ablating tissue.

Generally, one method for manufacturing a device with arbitrarily-shaped electrodes may be forming a device body from a nonconductive material, determining a shape for the electrode, forming the electrode from a conductive, biocompatible material in the determined shape, attaching an electrically conductive element (such as a trace or wire) to the electrode, affixing the electrically conductive element and the electrode to a section of the device, overmolding the electrode with an overmold material, and removing a portion of the overmold material above the electrode sufficient to expose the electrode. An arbitrarily-shaped electrode may also be formed by electrodepositing or sputtering conductive material on or in a depression or hollow formed on the device body, and may be connected to a conductive trace or wire by a via.

DETAILED DESCRIPTION OF PREFERRED EMBODIMENTS

Figure 1:
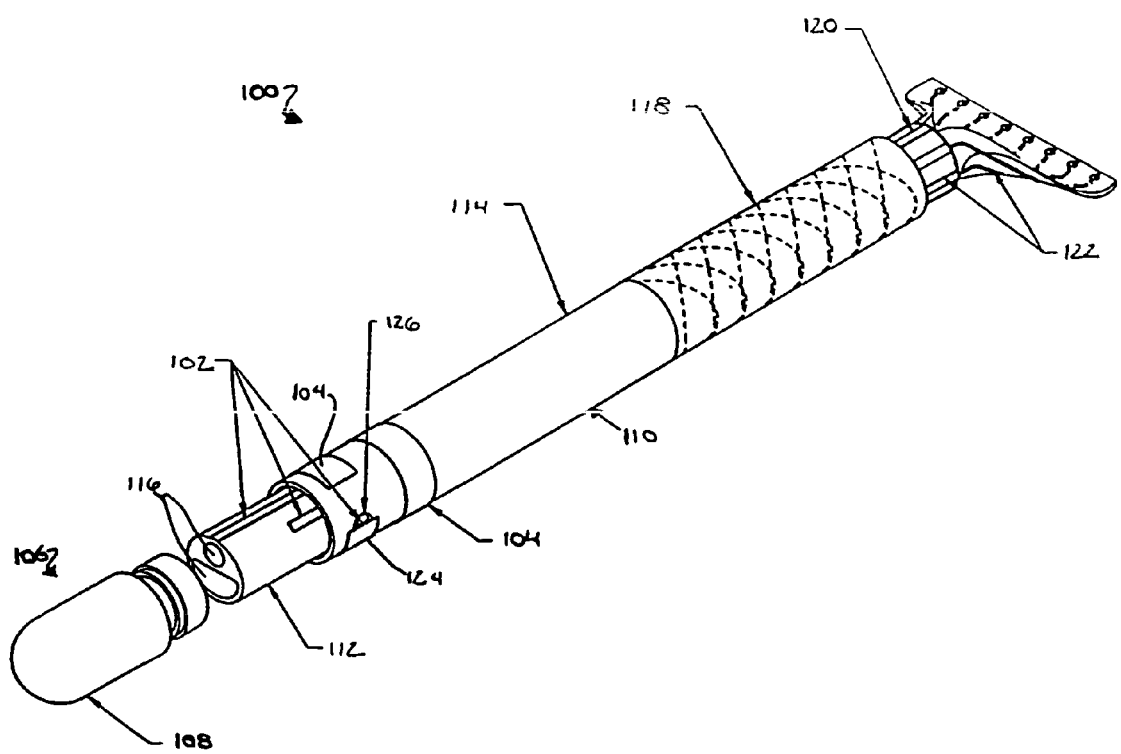
FIG. 1 depicts an isometric, partially-exploded view of a catheter having traces and electrodes integrated therein, in accordance with a first embodiment of the present invention.

Generally, one embodiment of the present invention takes the form of a medical device, such as a catheter or lead, having integrally formed electrodes and conductive elements. In this context, "integrally formed" refers to the fact that the electrodes and conductive elements are generally not mechanically affixed to the device, but instead are bonded thereto, formed on, or co-extruded with the device.

Exemplary medical devices include catheters and leads. As used herein, references to either a "catheter" or a "lead" are each intended to embrace the other term, unless specifically stated otherwise.

The medical device may conduct electricity generated by an apparatus attached to its proximal end to a contact site on its distal end (or to any point therebetween) by means of the integrally formed conductive elements. Energy may be delivered to the device's surface by electrically connecting a conductive element to an electrode. Generally, exemplary electrically conductive elements include metallic traces and wires. Energy may be conducted, for example, to necrotize or selectively damage tissue (also referred to as "ablation").

In addition to delivering energy to a contact site, a device embodying the present invention may also be used for diagnostic purposes. The electrodes or other contact sites formed along the exterior of the device may monitor bioelectric signals generated by tissue and transmit these signals along the previously mentioned traces or wires to a monitoring apparatus attached to the device's proximal end. These delivery sites may be located at the device's distal end or anywhere along its length. Alternative embodiments may include thermistors or thermocouples capable of monitoring temperature.

A portion of the device may include a braided material to impart additional stiffness and/or structural strength. For example, a portion of the device's exterior may have braids formed therein, while a separate portion of the device may lack such braids in order to permit more ready flexing. The braids may form a cross-hatch pattern to facilitate stiffness. Such braids may be made from a metal wire or a nonconductive fiber. One example of a nonconductive fiber suitable for use as a stiffening braid is Vectran. Vectran, or another nonconductive fiber, is typically used in place of metal wire if a via passes through the braided portion of the shaft and/or an electrode is formed on the outer surface of the shaft above the braided material. By employing a nonconductive fiber, the electrical signal along the via is not subject to interference, as it may be if a metal wire is used instead.

Additionally, the device may include an adapter. The adapter facilitates connection between the device and a diagnostic or energy-generating apparatus. The adapter generally includes embedded, conductive adapter traces that may connect the traces or wires inside the device to apparatus leads. The adapter shape (as well as the shape of the portion of the adapter mating with the apparatus) may vary. Further, the adapter may be enclosed within an outer shell or jacket. The jacket may protect the traces formed on the adapter, and also may include electrical connections facilitating the connection of a diagnostic or ablative apparatus to the device.

1. Embodiment of the Invention

FIG. 1 depicts a partially-exploded isometric view of a catheter 100 having traces 102 and electrodes 104 integrated therein, in accordance with an embodiment of the present invention. Generally, the catheter 100 includes at least one embedded or integrally formed, electrically conductive trace 102 or wire electrically connected to at least one electrode 104 formed on the outer surface of the catheter. Generally, an electrode 104 is formed in a depression 126, such that the outer surface of the electrode is flush with the catheter's outer surface. Typically, at least a portion of the catheter body is formed of an electrically nonconductive material.

In the view shown in FIG. 1, the catheter tip 106 (including tip electrode 108) is shown disconnected from the catheter shaft 110 in order to depict the traces 102, inner layer (in this case, a tube 112), and lumens 116. In operation, the tip 106 is affixed to the catheter 100.

As can be seen in FIG. 1, the present embodiment includes two nested layers, namely an inner catheter layer (or "tube") 112 and outer catheter layer (or "jacket") 114. As used herein, "jacket" typically refers to the outermost concentric layer of the device, while "tube" typically refers to an inner concentric layer. Generally, the term "layer" may refer to a tube 112 or jacket 114.

Generally, the catheter 100 may be made of multiple tubes 112 and/or jackets 114, concentrically nested. For example, the catheter may have two tubes, one inside the other, both of which are inside a jacket. Further, the catheter 100 may be made of multiple tubes 112 and/or jackets 114 spaced along the catheter's longitudinal axis. For example, three jackets may be spaced along the length of the catheter, each of which abuts an adjacent jacket. In other words, the catheter shaft 110 may be segmented, and may not consist of a single tube 112 or jacket 114 running along its entire length.

Figure 2:
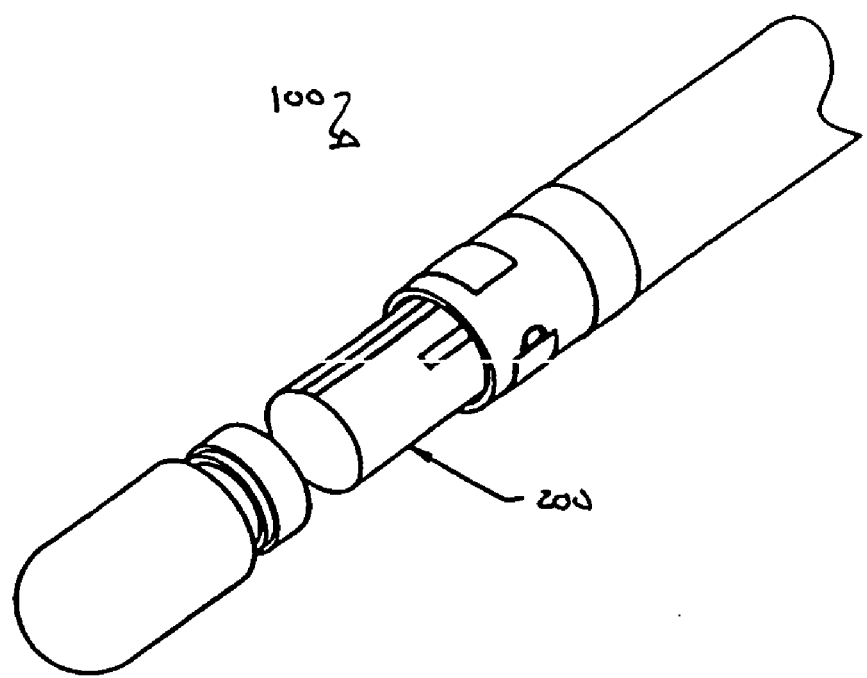
FIG. 2 depicts a fragmentary, isometric, partially-exploded view of a solid-core catheter having integrated traces and electrodes.

The tube 112 rests within the jacket 114, and is generally sized so that the outer surface of the tube contacts substantially all of the inner surface of the jacket. In other words, no longitudinal void space generally exists between the tube 112 and jacket 114 sidewalls. Void spaces may exist, however, where vias or passages are deliberately formed through a portion of the catheter 100. The tube 112 may be at least partially hollow (i.e., have one or more lumens 116) to allow incorporation of a steering mechanism, support deformable catheter segments, support fluid flow for cooling or providing an electrically conductive path to tissue, or permit passage of a lead or instrument therethrough. Alternatively, the tube 112 may have a solid core. FIG. 1 depicts a catheter with a partially hollow core (more specifically, with a bi-lumen tube 112), while FIG. 2 depicts a catheter 100 having a solid-core tube 200.

Returning to FIG. 1, electrically conductive traces 102 or wires are typically formed or placed on an exterior sidewall of the tube 112, while electrodes 104 are formed on the shaft 110 exterior. In one embodiment of the present invention, traces 102 may be formed on the exterior of the shaft 110. These traces may terminate in an electrode placed or formed on the jacket 114 exterior.

Alternatively, traces 102 may be formed on an inner sidewall of the jacket 114, or may be formed on an exterior sidewall of the tube 112, or may be embedded in either the jacket or tube. In yet another alternative embodiment, an externally-formed trace 102 may later be covered with a layer of nonconductive material to minimize signal interference.

In embodiments lacking externally-formed traces 102, each trace typically at least partially underlies an electrode 104. A via (not shown) may be formed from the underside of the electrode extending through the jacket 114 and to a trace 102, thus electrically connecting the electrode to the trace. This connection permits the trace to pass electrical energy from a medical device affixed to the outside of the catheter 100 at its proximal end to the electrode 104, or vice versa. The trace may be offset either along the longitudinal or lateral axes of the catheter from the electrode, so long as some portion of the trace remains in contact with the electrode.

Further, as shown in FIGS. 1 and 2, the geometry of a trace 102 and electrode 104 may vary widely. For example, the electrode 104 may be fully or partially cylindrical, forming a ring stretching partially or entirely around the circumference of the jacket 114. Regardless of electrode 104 shape, the trace 102 typically runs along the longitudinal axis of the catheter 100 at least to the edge of the electrode, but does not generally extend along the entire circumference of the tube 112. The trace may also have any cross-sectional shape desired. Accordingly, the lateral and longitudinal cross-sections of both the electrode 104 and trace 102 may vary, as may the depth or thickness of the trace and electrode.

In another embodiment, the outer surface of the tube 112 may include a trace 102 formed thereon. The trace extending along the tube's outer sidewall may conduct electrical energy from a connected apparatus to the electrode 104 formed on the outside of the jacket 114 (or anywhere along the shaft 110, in embodiments where the jacket only partially encapsulates the shaft), and vice versa. In yet another embodiment, the inner surface of the jacket 114 may include a trace 102 formed thereon. In such an embodiment, the outer surface of the tube 112 typically will not include any traces 102 in order to minimize the possibility of signal interference between two adjacent traces (i.e., one on the inner surface of the jacket 114 and one on the outer surface of the adjacent tube 112).

In the present embodiment, each trace 102 typically electrically connects to a single electrode 104. In this manner, discrete electrical signals are communicated between the electrode and any apparatus attached to the proximal end of the trace, minimizing or eliminating signal interference or cross-talk. If an apparatus controls or employs multiple sensory points through a single trace 102, then the trace in question may contact multiple electrodes 104.

Although reference has been made to a "trace" 102 above in describing embodiments, in some embodiments a single trace may be insufficient to carry the current necessary for diagnosis or operation. For example, when the catheter 100 is used to selectively necrotize or remove tissue (collectively referred to as "ablation" of tissue), more current may be required than a single trace 102 may carry. Accordingly, an alternative embodiment of the present invention may employ multiple traces 102 or electrically conductive wires in lieu of a single trace. Thus, throughout this document, the term "trace" should be understood to encompass multiple traces 102 or a wire, except where specifically disclaimed or such cross-reference renders the embodiment being discussed infeasible. Similarly, references to a "wire" should be understood to encompass a trace 102 or traces.

Continuing the discussion of FIG. 1, wire or nonconductive fiber of any suitable material (generally, "braided material" or "braided wire" 118) may be braided into a tube 112 section or portion of the jacket 114 to stabilize and stiffen the catheter. Alternatively, such braided material 118 may be co-extruded with a layer or placed between layers. Generally, this braided wire does not conduct energy during catheter operation, and is not operably connected to a trace 102 or electrode 104. Further, the braided wire 118 typically is embedded within the jacket 114, rather than placed along its surface where it may abrade tissue if inserted within a body. The braided wire may or may not be visible to the eye when the catheter shaft 110 is viewed. Accordingly, the wire 118 is shown in phantom in FIGS. 1 and 2. If the braid is placed in or along a portion of the device that may result in the braid electrically contacting a trace 102, via, or electrode 104, a suitable nonconductive material may be employed to minimize electrical cross-talk or signal interference. One such nonconductive material is Vectran.

The present embodiment may also include a connector or adapter structure 120. In its most general aspect, the adapter 120 includes one electrically conductive adapter trace 122 extension for each trace 102 within the catheter 100. The extension 122 mates with, aligns with, or otherwise operably connects to the trace, and extends directly or through a suitable electrical connection means to a plug, pin, or connector portion which, in turn, facilitates an electrical connection to a medical apparatus, such as a monitoring device. Accordingly, the adapter 120 assists in connecting the electrodes 104 on the catheter 100 to a medical device. The adapter is more fully discussed below with respect to FIG. 10.

The catheter tip 106 may be fabricated from a number of materials or material combinations, depending on the desired function of the catheter 100. For example, the catheter tip 106 may include one or more electrodes 104, or may be entirely covered by a single tip electrode 108, when the catheter is used for diagnostic or ablative purposes. Alternatively, where such functions are unnecessary, the catheter tip 106 may be formed from a non-conductive material, such as that used to form the jacket 114 or shaft 110, or may be simply metal-plated with no operable connection to any trace 102, wire, or electrode 104. Further, if a medical device such as a lead is passed through the catheter 100, the tip 106 may have an opening at its end, regardless of the material used to construct the tip.

In an alternative embodiment, the tip 106 may be formed of radiopaque material to permit detection of the tip during fluoroscopy or related procedures. The radiopaque material may alternatively be bonded to the inside or outside of the catheter 100, along the lumen 116, or may be embedded within the catheter walls. Further, the radiopaque material may be suspended within a polymer, or may be one or more solid, contiguous pieces of material. For example, the radiopaque material may take the form of fine particles suspended in a polymer tube, or may be a ring of radiopaque substance bonded to the inner surface of the jacket 114 or tube 112. Exemplary radiopaque materials suitable for use with the present invention include metals such as platinum, tungsten, gold, or other metals opaque to x-rays, or polymeric materials designed to be x-ray opaque.

The embodiment may also be provided with temperature sensing capabilities. For example, a thermistor 124 may be embedded or otherwise incorporated into the nonconductive jacket 114. The thermistor leads (in the case of a chip-style thermistor) may be attached to or come in contact with the aforementioned traces 102 in order to accurately convey temperature readings to an associated medical device at the proximal end of the catheter 100. Thermistors are typically placed in a depression 126 in order to keep the outer surface of the thermistor flush with the shaft 110 exterior.

Alternatively, a thermistor 124 may be located beneath or adjacent to an ablation electrode 104 in order to measure the electrode temperature during ablation. The thermistor may, for example, be placed in a depression 126 in the jacket surface and covered with a relatively thin layer of nonconductive material to prevent electrical interference. The electrode 104 may then rest above the thermistor 124, at least partially within the same depression 126 and connected to a trace 102 other than that operably connected to the thermistor. In this manner, the thermistor may measure the operating temperature of the electrode without interfering with the electrode's operation.

In yet another alternative embodiment, the thermistor 126 may be replaced by a thermocouple (not shown). In such an embodiment, thermocouple wires (for example, constantan and copper) may be incorporated into the jacket 114 or tube 112 during manufacture of the appropriate layer, or may be sandwiched between layers. If the wires are incorporated into a layer, they may be co-extruded with the layer. A depression 126 in the layer above the wires may permit exposure of the wires and formation of a thermocouple junction, as necessary. Again, an electrode 104 may be placed or formed within the depression 126 and the thermocouple may measure the temperature generated by the electrode to assist, for example, in monitoring tissue temperature experienced during ablation. If necessary, an electrically nonconductive (but heat conductive) layer may separate the thermocouple junction and electrode. Such a layer generally will withstand the temperature generated by the electrode 104 without deforming, warping, or suffering performance impairment.

A catheter 100, such as that of FIG. 1, may also incorporate a steering mechanism. A directional control mechanism of any type presently used may placed inside the catheter's lumen 116. Generally, at the distal end of the catheter 100, the directional control assembly is attached to the catheter tip 106. A wire or directional guide is affixed to a steering mechanism located at or outside the proximal end of the catheter. The control assembly may be affixed to the catheter tip 106 in a variety of manners, including solvent adhesion, sonic welding, co-extrusion, and so forth. Alternatively, the tip may be formed or extruded around the control assembly, after which the entire tip structure may be affixed to the jacket 114 or tube 112. In yet another embodiment, the catheter 100 may be provided with a fluid-steerable armature.

Figure 3:
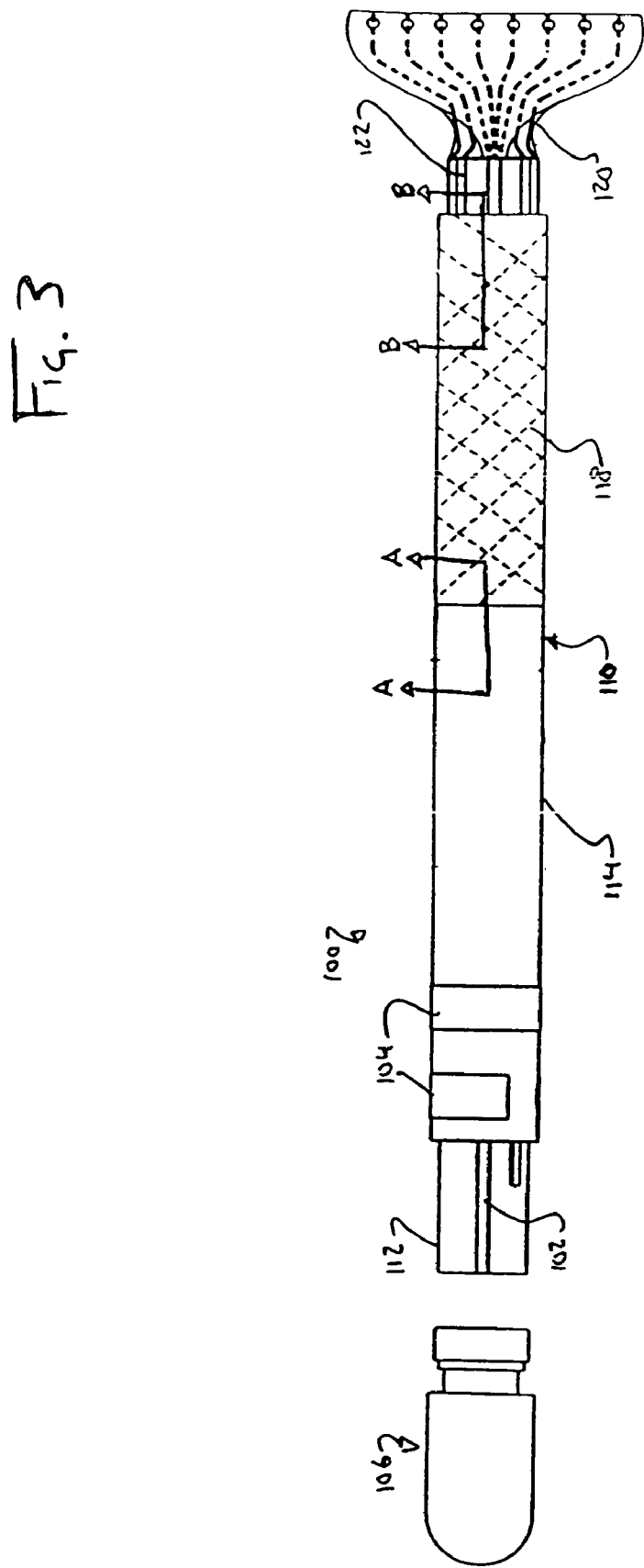
FIG. 3 depicts a partially-exploded side view of the catheter of FIG. 1.

FIG. 3 depicts a side view of the catheter 100 of FIG. 1. The braided material 118 incorporated into the catheter, outer jacket 114, adapter 120, and electrodes 104 may be clearly seen. Further, because the tip 106 is shown disassociated from the catheter shaft 110, a portion of the tube 112 and a trace 102 are also visible.

Generally, as shown in FIG. 3, the electrodes 104 formed on the surface of the catheter are relatively flush with the outer sidewall of the jacket 114. The electrodes 104 may extend slightly beyond the jacket 114 surface, or alternatively may be slightly recessed, so long as the edge formed by such extension or recession does not create a discontinuity between surfaces sufficient to abrade or damage tissue. The electrodes 104 are generally formed on the jacket 114 surface, and are integral to the catheter.

Still with respect to FIG. 3, the adapter 120 is shown without an outer jacket. An outer jacket may be placed around the adapter 120 to protect the adapter traces 122 from damage, as well as to minimize electrical signal noise or degradation resulting from electrical currents in tissue adjacent to the catheter. Generally, the diameter of the adapter 120 plus the adapter jacket is approximately equal to the catheter 100 diameter.

Figure 4:
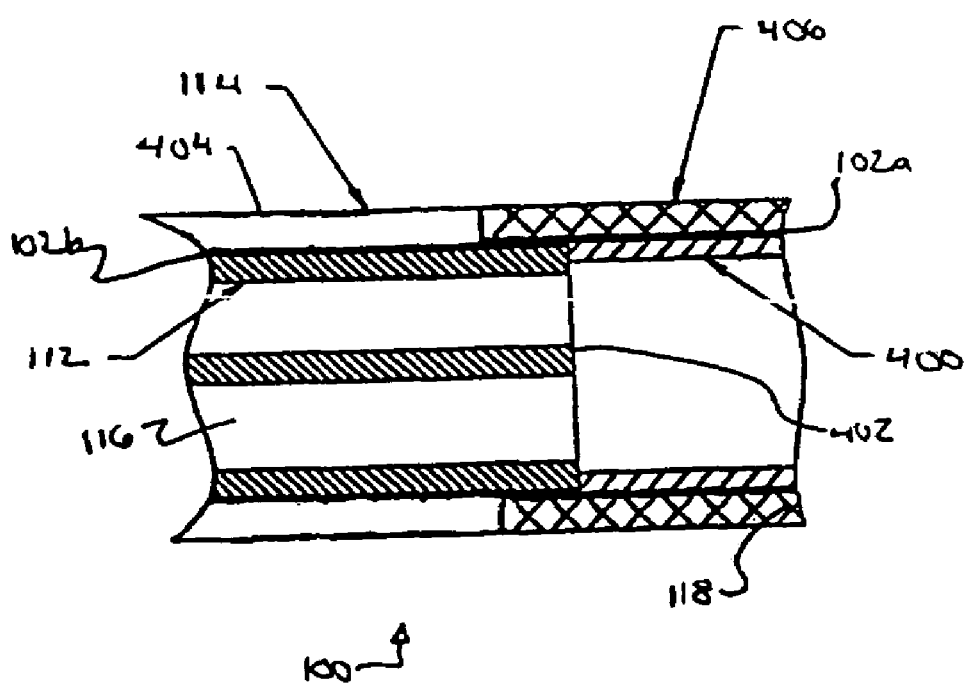
FIG. 4 depicts a fragmentary, cross-sectional view taken along line A-A of FIG. 3.

FIG. 4 depicts a cross-sectional view of a portion of the present embodiment, taken along line A-A of FIG. 3. As mentioned with respect to FIG. 1, the present catheter 100 has a bitumen tube 112. Generally, the tube 112 may extend only partially along the length of the catheter 100. An inner layer 400, as shown, may extend along a portion of the catheter interior. When fully assembled, the tube 112 may abut the inner layer 400. This inner layer 400 may be a separate, adjacent tube, for example. The combination of inner layer 400 and tube 112 defines a passage throughout the length of the catheter 100. When a tube having multiple lumens 116 is employed, as with the embodiment shown in FIGS. 1 and 4, the meeting point between the inner layer and tube may define the separation of a single passage (i.e., the inner layer interior) into multiple passages (i.e., the tube interior).

Also generally, the inner layer 400 (if present) underlies the outer jacket 114, and may impart additional structural strength to the catheter 100. The inner layer 400 may also create a stair-step profile in combination with the outer jacket 114, facilitating electrical connection between adjacent elements of the catheter shaft 110. The stair-step profile of the inner layer and outer jacket combination may also aid in resisting shear force applied to the catheter 100. Further, the combination of inner layer and outer jacket may provide convenient support and protection to traces 102 disposed therebetween during operation and manufacture of the device. (The manufacture of an embodiment is disclosed in further detail below, in the section entitled "Method of Manufacture.") It should be noted that the inner layer 400 is entirely optional. Alternative embodiments may omit the inner layer and simply extend the tube 112 along the length of the catheter.

Also depicted in FIG. 4 is the transition between an inner layer 400 and the bitumen tubing 112. In an embodiment having a single lumen tube, no internal divider 402 separating the lumens would be present. Similarly, in an embodiment having a solid core tube 200 with no lumen (as shown in FIG. 2, for example), no passage would be seen.

As shown in FIG. 4, the device's outer jacket 114 may be made of multiple, abutting elements 404, 406 instead of being made from a single piece. When the outer jacket 114 is made of multiple elements (i.e., is segmented), one or more outer jacket elements 406 may include braided wire or nonconductive fiber 118, as discussed above and shown in FIG. 4. Generally, the transition point between two adjacent outer jacket elements 404, 406 is substantially smooth. In other words, very little or no discontinuity between outer jacket elements 404, 406 is formed on the catheter 100 or lead exterior when the elements are bonded to one another to form a contiguous jacket 114.

The inner layer 400 and tube 112, by contrast, may or may not abut one another in an assembled catheter 100 or lead. A slight gap between the tube 112 (or bi-lumen tubing, as shown in FIG. 4) and inner layer 400 may be present in some embodiments. In alternative embodiments, the inner layer and tube may be closely toleranced to ensure the end walls of each abut. It should also be noted that the inner layer 400 may be made of multiple elements, in a manner similar to the outer jacket 114.

Further, although the terms "inner layer" 400 and "outer jacket" 114 are used, an alternative embodiment may employ a single jacket having a stair-step portion corresponding to the positioning of the inner layer or may omit the inner layer entirely. Accordingly, a single-jacket design may be used in some embodiments of the present invention.

In yet another alternative, and as also shown in FIG. 4, an outer jacket 114 having internally formed traces 102a may be paired with a tube 112 or lumen having externally formed traces 102b. Essentially, multiple fragmentary traces may be created, each running longitudinally along a portion of the catheter. In order to maintain an unbroken electrical connection, each fragmentary trace 102a, 102b typically at least partially overlaps an adjacent fragmentary trace. Generally, and starting at the proximal end, a jacket trace 102a may be connected with a tube trace 102b, which in turn is operably connected to an electrode 104 through a via. Accordingly, the trace 102 may be formed anywhere within the tube 112, thus imparting a greater degree of freedom in placing the trace.

Similarly, where multiple tubes 112 or jackets 114 are employed, each longitudinally adjacent tube or jacket may have a trace 102 formed thereon. These traces may abut one another within the catheter 100, providing a contiguous path for transmission of electrical energy.

In the embodiment of FIG. 4, a first fragmentary trace 102a is formed between the inner layer 400 and a first outer jacket segment 406. Generally, this trace 102a may be formed along the interior sidewall of the first outer jacket segment 406, the exterior sidewall of the inner layer 400, embedded within either jacket, or may be a multi-part trace partially formed on the inner layer and partially on the outer jacket. A method for forming traces 102 is discussed in more detail below.

In addition to the first fragmentary trace 102a underlying or formed within the outer jacket 114, a second fragmentary trace 102b extends along the tube 112. As with the first fragmentary trace 102a, the second fragmentary trace 102b may be formed on the interior sidewall of the second jacket segment 404, within the jacket, within the tube 112, along the exterior sidewall of the tube, or on any combination of the above. Essentially, the second fragmentary trace 102b may be formed anywhere that permits it to electrically contact the first fragmentary trace 102a.

Figure 5:
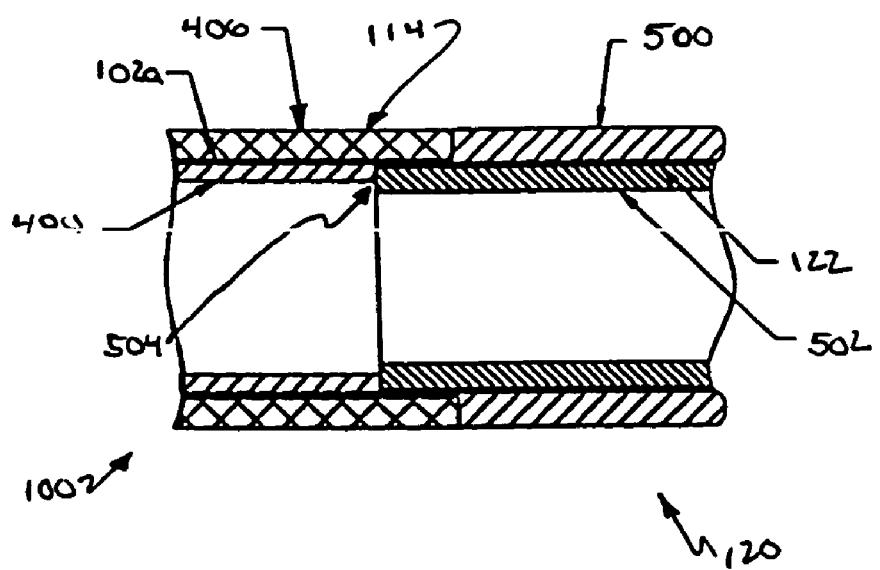
FIG. 5 depicts a fragmentary, cross-sectional view taken along line B-B of FIG. 3 and also including an optional adapter outer jacket.

FIG. 5 depicts a cross-sectional view of a portion of the catheter 100 and adapter 120 taken along line B-B of FIG. 3. In this cross-section, the adapter 120 includes the optional outer jacket 500 previously mentioned, as well as an adapter inner layer 502. As with FIG. 4, FIG. 5 shows the first fragmentary trace 102a running along the first outer jacket segment 406. Here, however, the first fragmentary trace 102a terminates at or near a portion of the adapter 120 having an adapter trace 122. Generally, the adapter includes multiple adapter traces 122 spaced along its circumference (or, in the case of a non-circular adapter, its edges). The adapter trace 122 electrically contacts the first fragmentary trace 102a, completing an electric current path from an electrode 104 (not shown) on the catheter shaft 110, along the second fragmentary trace 102b (not shown), through the first fragmentary trace 102a, and along the adapter trace 122 to a connector (not shown) for a diagnostic or ablative apparatus.

As also shown in FIG. 5, the inner layer 400 typically terminates closer to the distal end of the catheter 100 than does the outer jacket segment 406. The resulting shoulder 504 formed by the inner layer 400 and outer jacket 114 terminates movement of the adapter 120 into the interior of the catheter beyond the shoulder, thus facilitating properly positioning the adapter trace 122 for longitudinal alignment with the catheter trace 102a. Of course, this stair-step configuration 504 may be formed in reverse, with the inner layer 400 terminating closer to the proximal end of the catheter than the outer jacket 114, and achieve similar results.

Although not shown, an alternative embodiment may include a groove or slot in either the catheter 100 or adapter 120 and a matching fin or extension in the other element. By aligning the fin with the groove, the adapter 120 and catheter 100 may be properly laterally aligned for electrical connection of a catheter trace 102 to an adapter trace 122. In yet another embodiment, markings along the outside of the catheter and/or adapter may serve the same purpose.

2. Embodiment Having Multiple Inner Layers

In addition to the embodiments described above, another embodiment of a catheter 600 may have multiple inner, concentric layers nested within or beneath the jacket 114. For example, a single catheter 600 may have an outer jacket 114, an outer tube 602, and an inner tube 604, as shown in a partially-exploded view in FIG. 6. Each layer (jacket, outer tube, and inner tube) may include a different type of electrically conductive element or may include electrically conductive elements in different alignments.

For example, the outer jacket 114 may have one or more electrodes 104 positioned along and extending through its outer sidewall, the outer tube 602 may have one or more traces 102 operably connected to such electrodes 104, and the inner tube 604 (also referred to as a "lumen tube") may have yet another trace or traces 102 operably connected to different electrodes 104. In an embodiment including a tip electrode 108 formed on the catheter tip 106, traces along or embedded within any or all of the aforementioned layers (i.e., jackets and/or tubes) may connect to the tip electrode 108.

Since the jacket 114 and tubes 602, 604 are typically made of nonconductive material, traces 102 may run along or within each layer without electrically contacting one another, so long as a first trace does not run along an exterior sidewall of a first layer and a second trace run along an interior sidewall of an adjacent, concentric second layer. Longitudinally aligning traces 102 in this manner may be advantageous where multiple contact points or electrodes 104 are longitudinally aligned along the catheter surface. By separating longitudinally aligned traces with a layer of nonconductive material or placing such traces in different layers 114, 602, 604, each electrode 104 in the aforementioned alignment may be in electrical contact with a trace 102, without disrupting signals passing through another trace.

Figure 6:
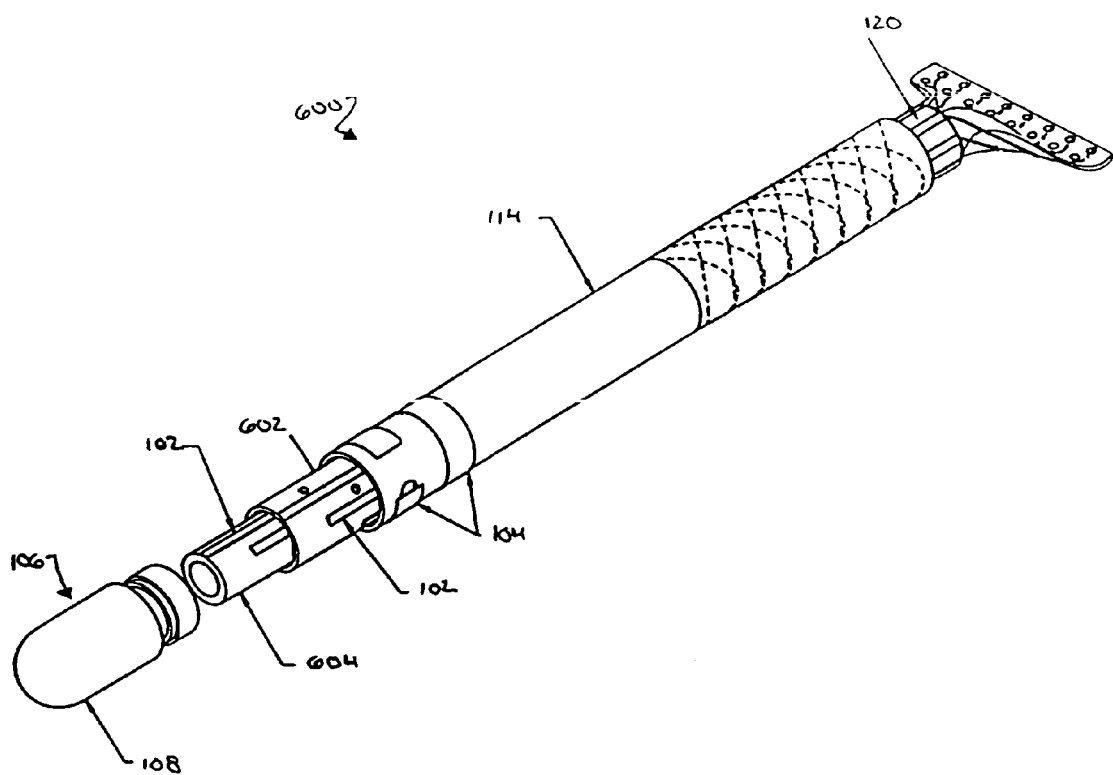
FIG. 6 depicts an isometric, partially-exploded view of a single catheter having integrated traces and electrodes and multiple catheter layers, namely an outer jacket, an outer tube, and an inner tube.

As with the embodiment of FIG. 1, any tip type or type of tube disclosed herein may be used with the embodiment of FIG. 6.

Figure 7:
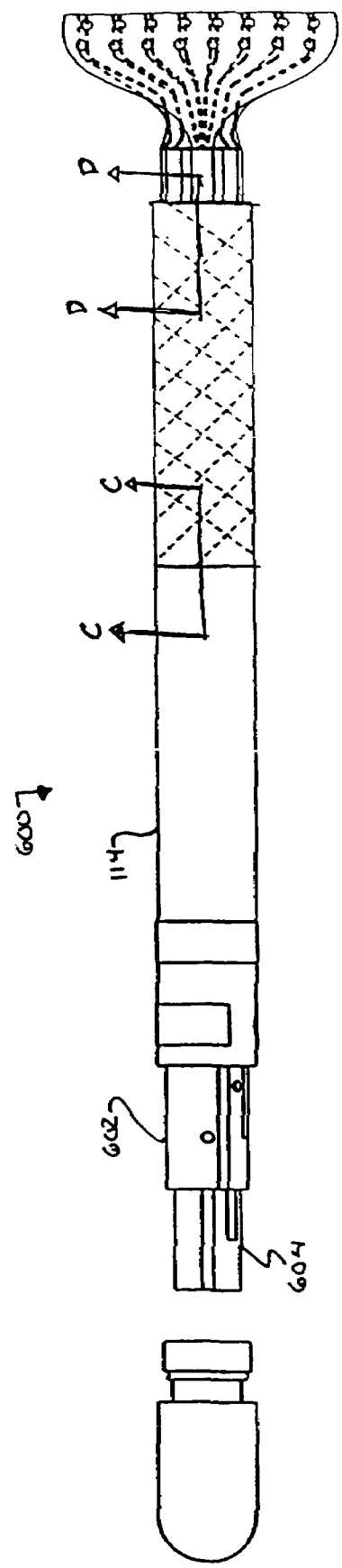
FIG. 7 depicts a partially-exploded side view of the catheter of FIG. 6.

FIG. 7 depicts a side view of the catheter 600 of FIG. 6, showing the outer jacket 114, outer tube 602, and inner tube 604.

Figure 8:
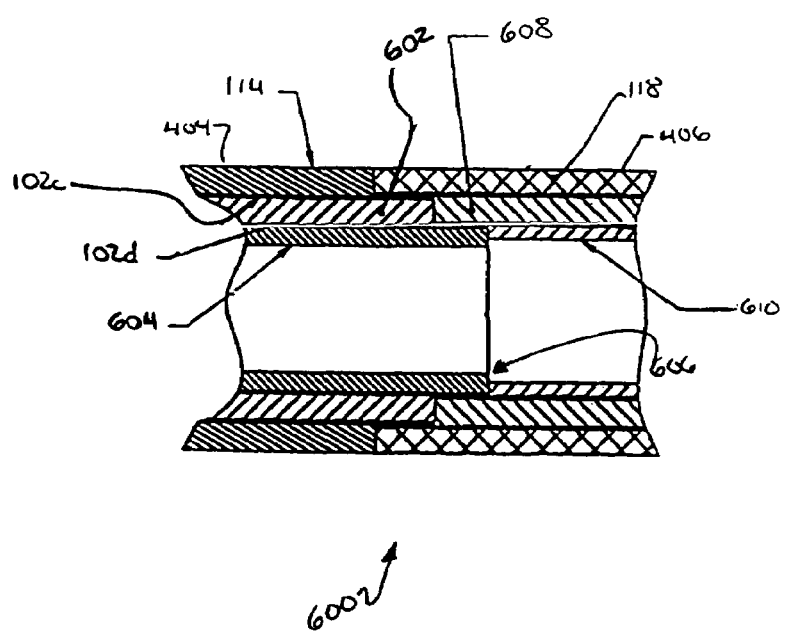
FIG. 8 depicts a fragmentary, cross-sectional view of the catheter of FIGS. 6 and 7, taken along line C-C of FIG. 7.
Figure 9:
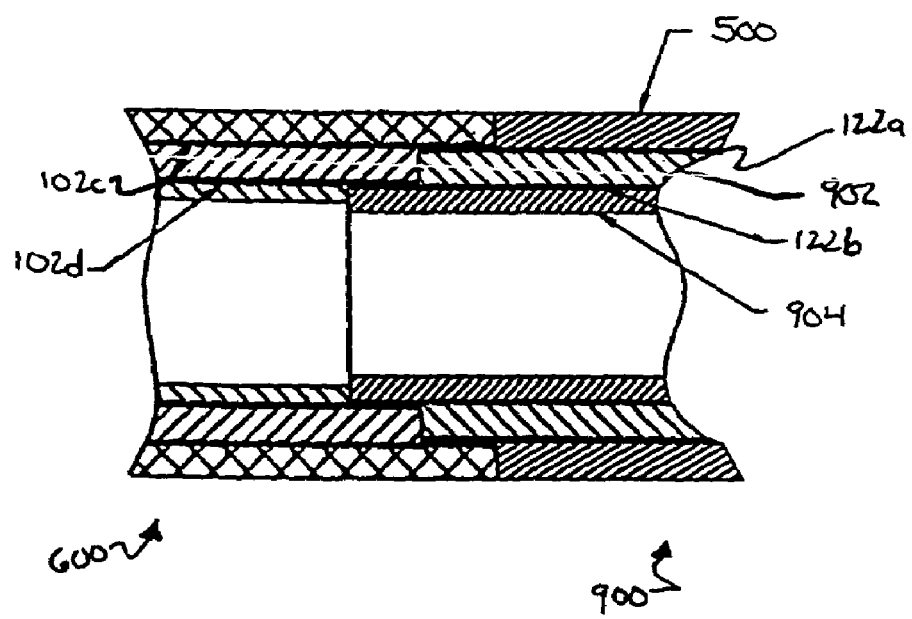
FIG. 9 depicts a fragmentary, cross-sectional view of the catheter of FIGS. 6 and 7, taken along line D-D of FIG. 7.

FIGS. 8 and 9 depict cross-sectional views of the present embodiment 600 taken along lines C-C and D-D, respectively, of FIG. 7. Generally, these views are similar to those shown in FIGS. 4 and 5, but depict in cross-section both the inner tube 604 and outer tube 602 of the present embodiment, as well as multiple traces 102c, 102d longitudinally aligned with one another. For example, FIG. 8 depicts a first trace 102c, initially positioned between the outer jacket 114 and outer tube 602, and a second trace 102d, initially positioned between the outer tube and inner tube 604. In this instance "initially positioned" refers to the position of the trace with reference to the leftmost portion of the figure, i.e., towards the distal end of the catheter 100. The first and second traces 102c, 102d each may be made up of multiple trace fragments, as discussed above in more detail with respect to FIG. 4.

As with the embodiment of FIG. 4, the outer jacket 114 of the present embodiment 600 may be made of multiple outer jacket segments 404, 406. These segments may be bonded to one another, or may each be bonded to the layer directly beneath them. Further, braided material 118 may be included in an outer jacket segment 406.

Similar to the single-tube catheter 100 discussed with reference to FIGS. 1 through 4, the present embodiment 600 includes a shoulder configuration 606. Part of this shoulder 606 is formed by a first inner layer 608, which abuts the first tube. Here, however, a second inner layer 610 forms a second portion of the shoulder 606 for contact with the inner tube 604 defining the lumen 116. This second shoulder portion is optional, but may provide additional security with respect to properly seating a tube. Further, the second shoulder assists in properly aligning any inner tube traces 102d within the catheter assembly.

FIG. 9 depicts a cross-sectional view of a multi-layer adapter 900 connected to the catheter 600. Multiple adapter traces 122a, 122b may be longitudinally aligned between or within the various adapter layers (such as the adapter outer jacket 500, adapter first inner layer 902, and adapter second inner layer 904) while maintaining electrical separation of the traces. Each adapter trace 122a, 122b generally aligns with and connects to a catheter trace 102c, 102d. Generally, the multi-layer adapter 900 operates in the same manner as the standard adapter, discussed below.

3. Adapter

Figure 10:
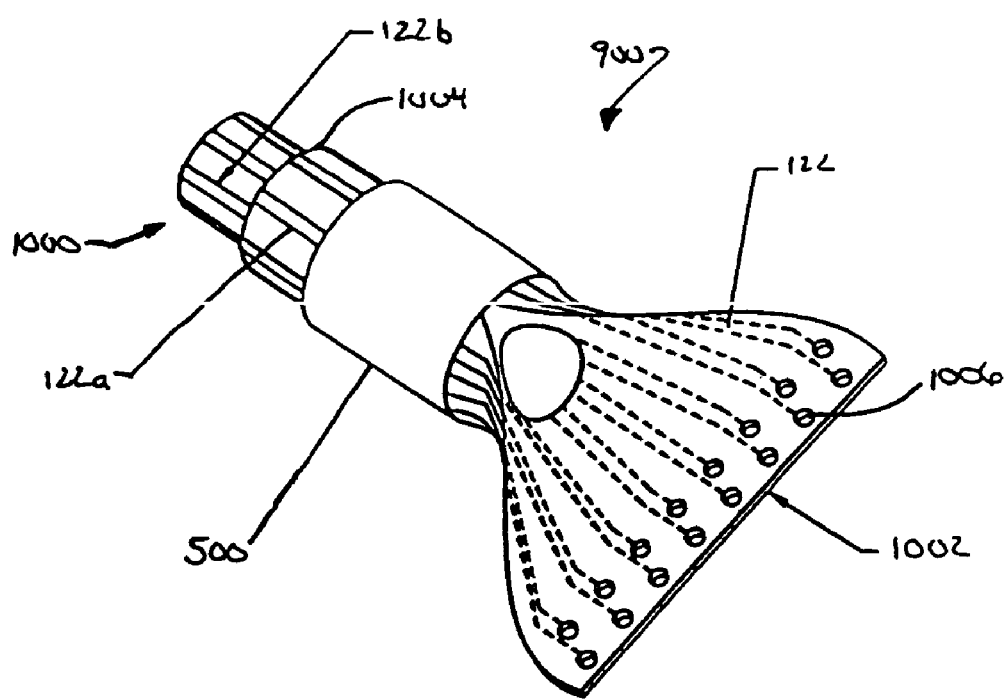
FIG. 10 depicts an isometric view of an adapter having a planar end.

FIG. 10 depicts an isometric view of the adapter 900 mentioned in the discussion of FIGS. 6-9. Generally, this adapter embodiment differs from the embodiment 500 shown in FIGS. 1-5 in that it includes dual layers of longitudinally aligned adapter traces 122a, 122b. The mating of the adapter 900 with the catheter 600 was previously discussed with respect to FIGS. 1, 5, and 9. The adapter 900 is shown with an outer jacket 500.

Typically, the adapter outer jacket 500 is formed from a nonconductive material that may or may not be identical to the material used to form the catheter shaft 110. The adapter traces 122a, 122b may be exposed on the plug portion 1000 of the adapter (i.e., the portion of the adapter fitting within the catheter). Typically, these traces are concealed within the nonconductive catheter shaft 10 once the adapter 900 is mated with the catheter 600. Further, the traces 122a, 122b are generally embedded within the nonconductive material of the adapter jacket 500 and adapter tail 1002. In FIG. 10, such embedded traces are shown in phantom on the adapter tail 1002. The plug portion 1000 is generally shaped to include one or more steps 1004 designed to abut the aforementioned jacket shoulder(s) within the catheter 600. At least a portion of each adapter trace 122a, 122b is exposed in order to permit the adapter trace to mate with the corresponding catheter trace 102. Typically, the adapter traces are circumferentially aligned with the catheter traces. The width and thickness of both adapter traces 122a, 122b and catheter traces 102 may be tailored to ensure the maximum electrical energy necessary for diagnosis or ablation may be delivered to a target site without physically affecting any portion of the catheter or adapter.

The adapter body 900 may transition from a cylindrical shape to a planar shape. The cylindrical portion (i.e., the adapter jacket 500 portion and plug portion 1000) matches the catheter shape, while the planar connection structure 1002 (the "fan tail" shape shown in FIG. 10) facilitates connecting a diagnostic or other medical apparatus and a catheter trace through one or more connection points, such as holes 1006 (as shown) or prongs. Further, the adapter tail 1002 may split laterally, along the longitudinal axis of the tail, to permit attachment to an apparatus having connectors so aligned.

Figure 11:
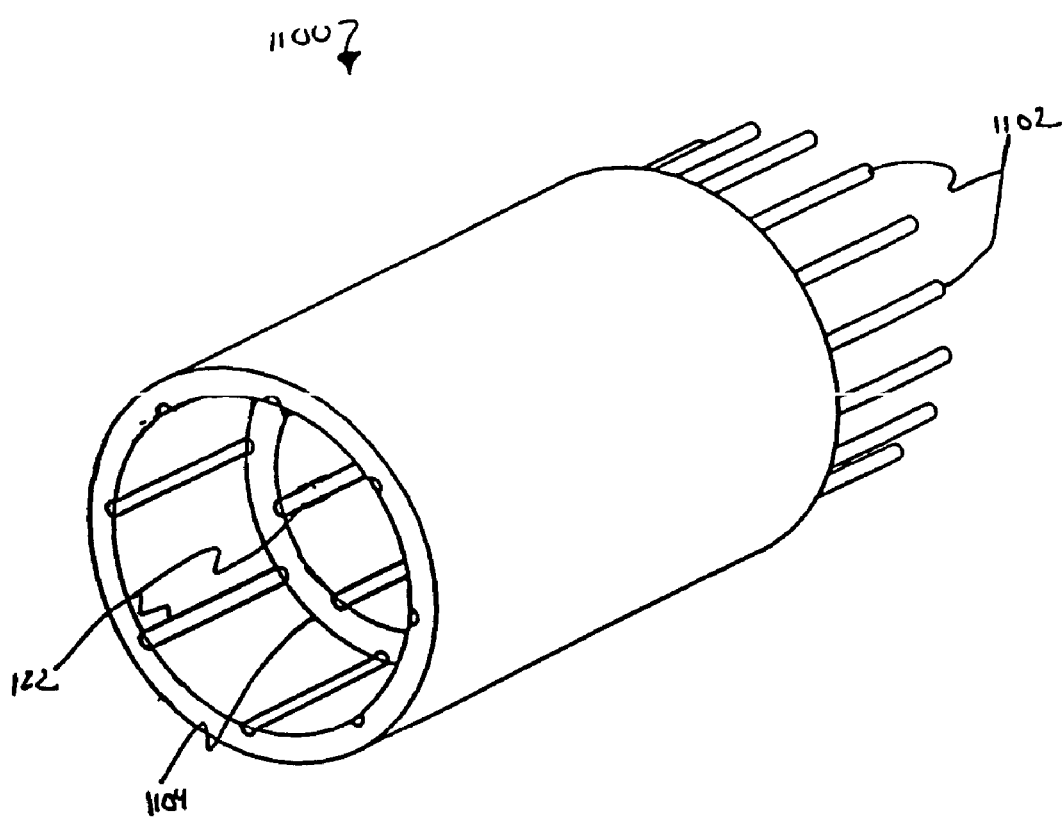
FIG. 11 depicts an isometric view of an cylindrical embodiment of an adapter.

FIG. 11 depicts an alternative embodiment of an adapter 1100. In this embodiment, the adapter 1100 lacks the planar structure, or fan tail 1002, of the embodiment 900 shown in FIG. 10. Instead, the adapter traces 122 terminate in conductive prongs 1102 extending rearwardly from the adapter. Further, unlike the adapter 900 of FIG. 10, the present adapter 1100 has a reverse stair-step configuration 1104 at the end designed to mate with the catheter. Accordingly, rather than inserting a portion of the adapter into a catheter 100, the catheter is at least partially inserted into the adapter. This requires the distal end of the catheter 100 to have a mating stair-step protrusion. The shoulder 1104 inside the adapter 1100 longitudinally aligns the catheter with the adapter. It should be noted that either type of adapter (one having a fan tail or cylindrical prong arrangement) may be used with either catheter mating configuration.

Figure 12:
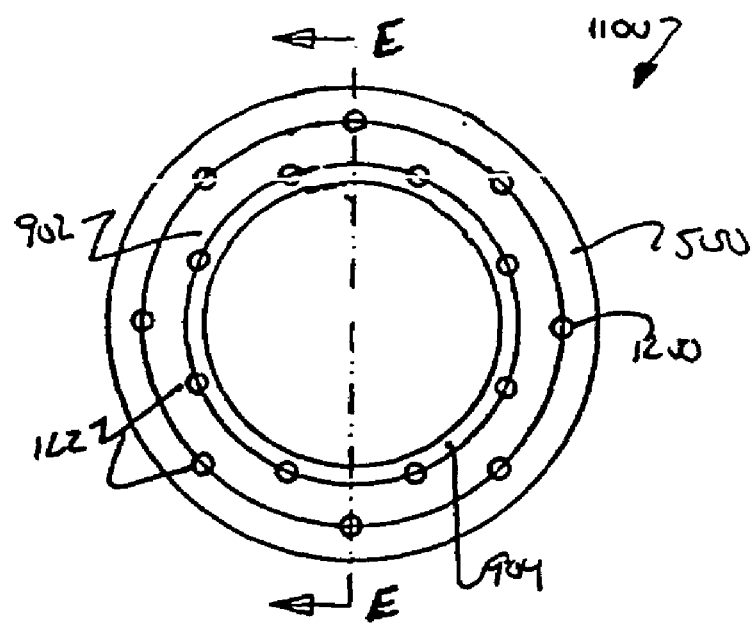
FIG. 12 depicts the cylindrical adapter of FIG. 11, as viewed from the mating end.

FIG. 12 depicts the adapter 1100 of FIG. 11, as viewed from the distal end. (i.e., the end mating with a catheter 100). As can be seen, the adapter 1100 may have multiple layers of traces 122 making up the connection structure, each designed to mate with multiple layers of traces 102 in the catheter. These multiple trace layers may be offset, as shown in FIG. 12, or aligned with one another without affecting the operation of the catheter or adapter. Further, it should be noted that the adapter traces 122 are all shown as round in cross-section. In order to expose the adapter traces 122, a portion of each trace is removed such that the remainder of the trace is flush with the inner sidewall of the outermost layer in which the trace is formed (i.e., the outer jacket 500, adapter first inner layer 902 or adapter second inner layer 904). For example, adapter trace 1200 sits between the outer jacket 500 and adapter first inner layer 902. Accordingly, the adapter trace 1200 is flush with the inner sidewall of the outer jacket 500. The adapter trace 1200 is fully circular in cross-section for its length between the outer jacket 500 and adapter first inner layer 902.

Figure 13:
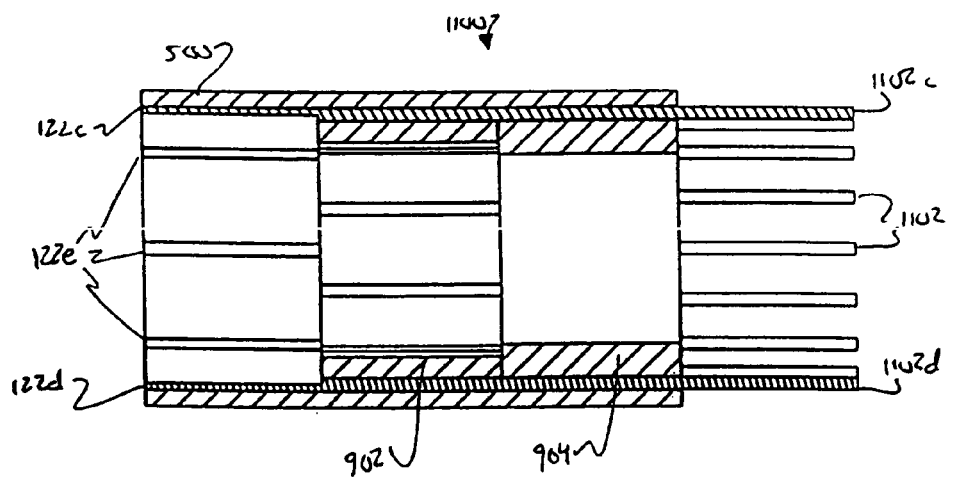
FIG. 13 depicts a cross-sectional view of the cylindrical adapter of FIGS. 11 and 12, taken along line E-E of FIG. 12.

FIG. 13 depicts a cross-sectional view of the cylindrical adapter 1100, taken along line E-E of FIG. 12. Two adapter traces 122c, 122d are shown in fine diagonal shading; these traces extend along the body of the adapter and terminate in conductive prongs 1102c, 1102d. The entirety of the trace/prong structures are diagonally shaded. For contrast, non-conductive material making up the various adapter layers 500, 902, 904 is shown in broader shading. The shoulder formed by the stair-step configuration 1104 of the adapter sidewall may also be seen. The adapter outer jacket 500, first inner layer 902, and second inner layer 904 may also be seen.

In the side view of FIG. 13, the adapter traces exposed on the inner sidewall of each adapter layer are shown. For example, one set of traces 122e may be seen extending along the outer jacket's 500 inner sidewall. These traces are hidden by the sidewall of the adapter first inner layer 902. Each of the adapter traces 122 generally terminates in a conductive prong 1102.

An adapter may include color-coding along its connection structure (either fan-tail 1002 or cylindrical prong 1102), identifying each wire or adapter trace 122 operably connected to the structure. However, because the adapter 900, 1100 is designed to mate with a connecting cable (which, in turn, connects to an input or output of a medical device), the pin-out or arrangement of the connection structure generally connects the appropriate catheter trace 102 to the appropriate input or output without requiring the user to identify individual traces. In alternative embodiments, the adapter may directly connect with a medical device, thus eliminating the intermediate connector cable.

Additionally, the "fan-tail" shape of the adapter 900 facilitates incorporating an access port (not shown) to permit leads, instruments, steering mechanisms, and so forth to pass into the adapter, into the catheter, and down the lumen 116 (if any) running the length of the catheter. In this manner, such items may be easily inserted into the catheter body without interfering with the adapter's operation. Handle mechanisms to control steering mechanisms, medical devices attached to leads or instruments, and so forth may be attached to the appropriate element outside the adapter body.

4. Catheter Having Embedded Wires

Figure 14:
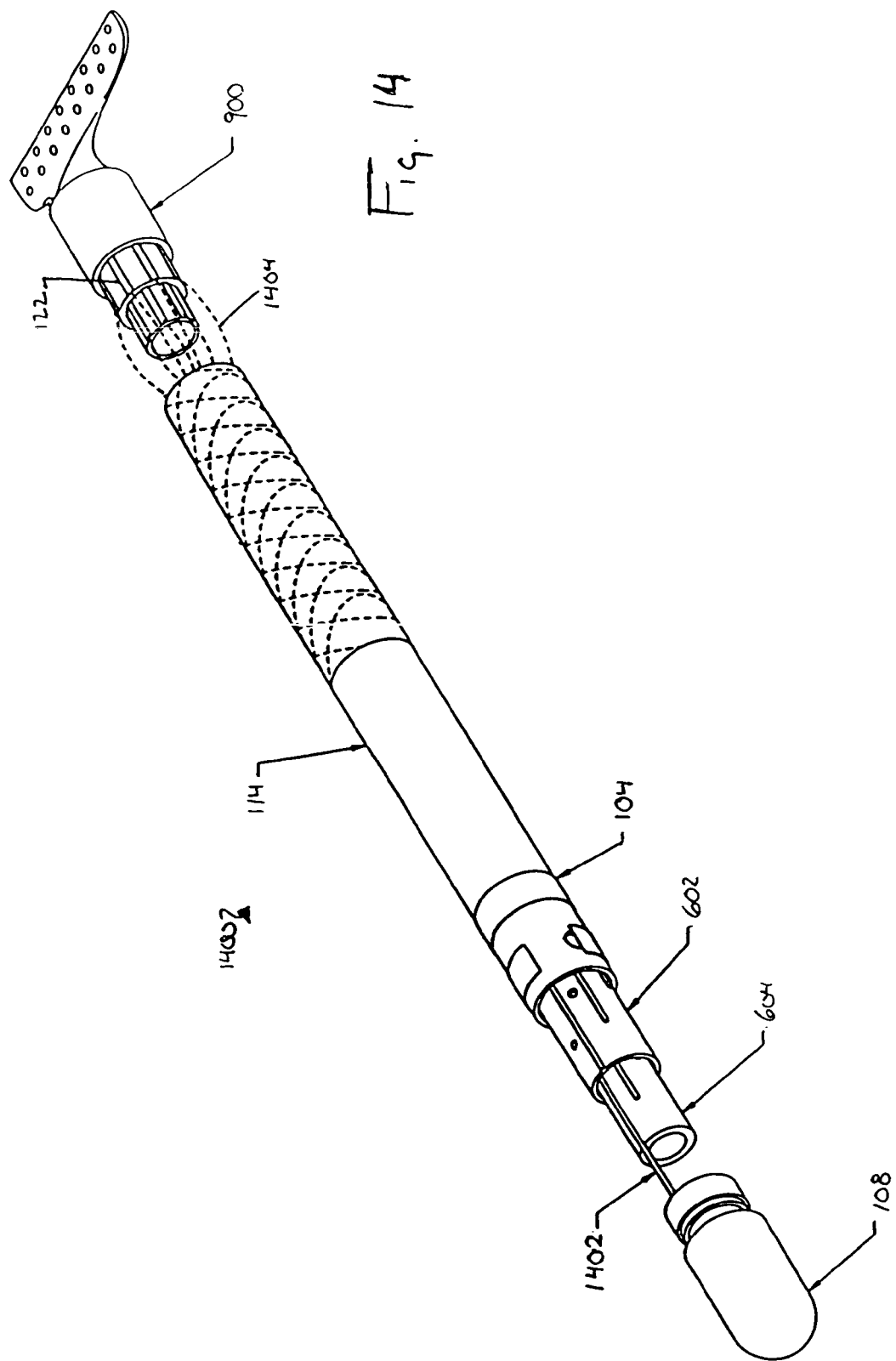
FIG. 14 depicts an isometric, partially-exploded view of a catheter having embedded wires in lieu of traces.

FIG. 14 depicts yet another embodiment of the present invention, namely a catheter 1400 having embedded wires 1402 in lieu of traces 102. Wires may be formed or embedded along the catheter when significant amounts of electrical energy must be delivered between an attached apparatus and an electrical contact point on the catheter surface. One such application that may require the use of a conductive wire 1402 instead of a trace 102 is tissue ablation. The general physical structure of the catheter layers (i.e., the outer jacket 114, outer tube 602, and inner tube 604) is similar to the catheter 600 depicted in FIG. 6.

The catheter 1400 shown in FIG. 14 is partially exploded. Accordingly, a wire 1402 connected to the tip electrode 108 may be seen. Illustrative connections 1404 between the catheter shaft 110 and adapter 900 are also shown. In one embodiment, these connections 1404 are soldered, and generally connect each adapter trace 122 to a corresponding wire 1402. Soldering may also be used in previously-discussed embodiment to secure an adapter to a catheter and connect adapter traces to catheter traces.

Figure 15:
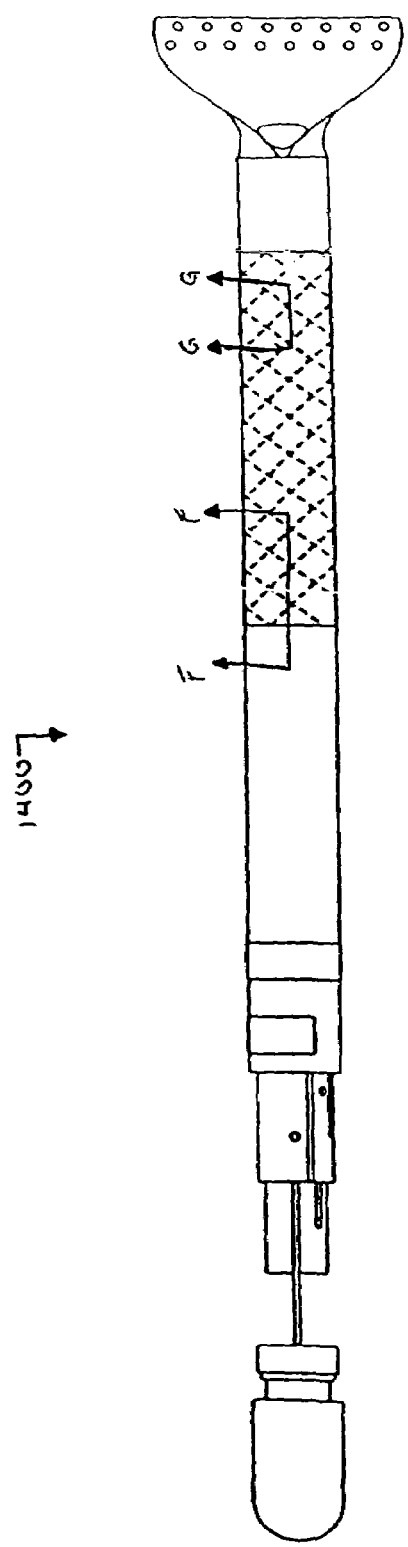
FIG. 15 depicts a partially-exploded side view of the catheter of FIG. 14.

Generally, the wire 1402 operates in much the same manner as the aforementioned trace. It serves as a conduit for electrical energy between an electrode 104 and apparatus. The wire may be co-extruded with the catheter 1400, or may be placed within a depression (not shown) formed on or in a catheter layer (i.e., jacket or tube). One or more wires 1402 may run any length of the catheter 1400, as necessary. Typically, the wires are sufficiently flexible to permit the catheter to bend and/or be steered by a control apparatus. FIG. 15 depicts a side view of the catheter 1400 of FIG. 14.

Figure 16:
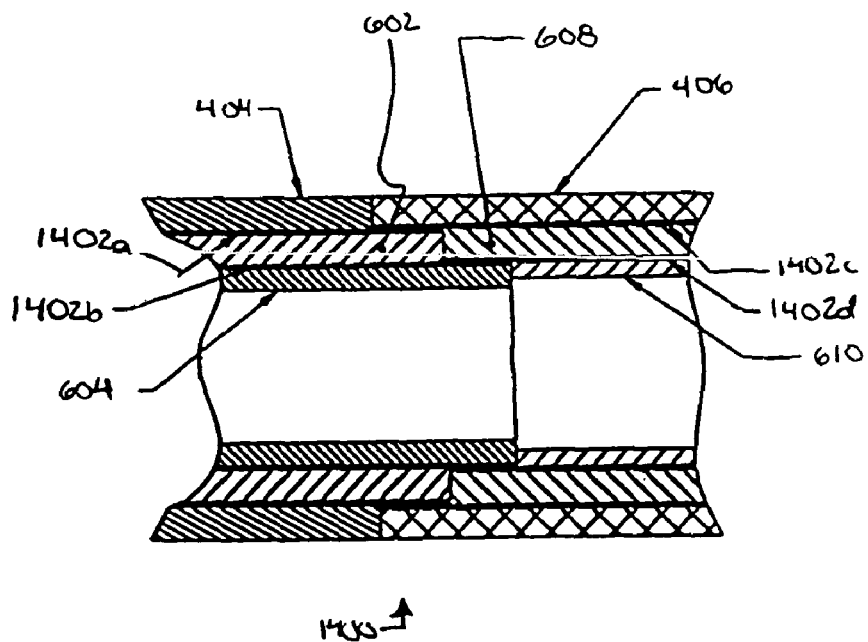
FIG. 16 depicts a fragmentary, cross-sectional view of the catheter of FIGS. 14 and 15, taken along line F-F of FIG. 15.
Figure 17:
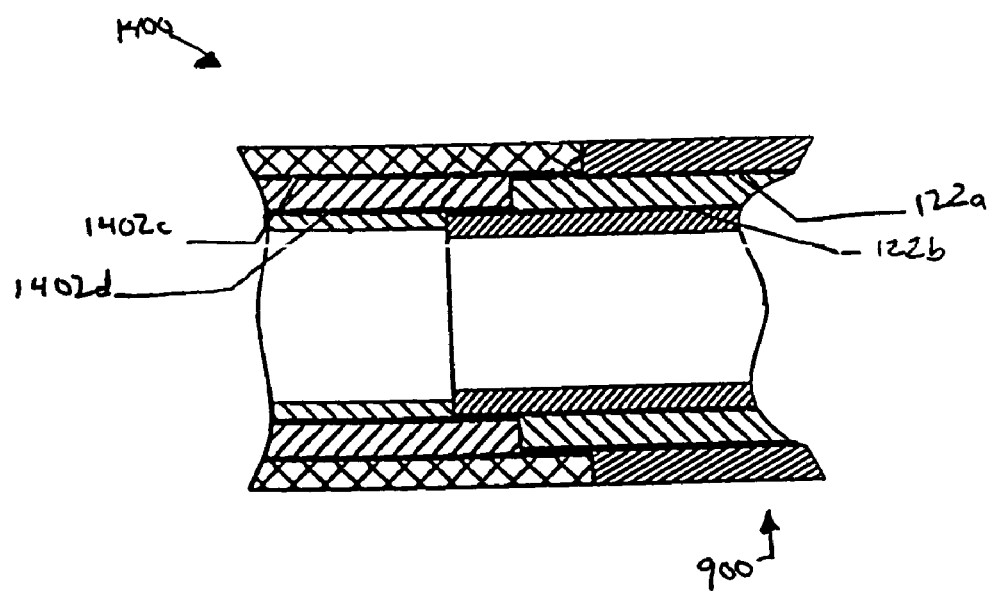
FIG. 17 depicts a fragmentary, cross-sectional view of the catheter of FIGS. 14 and 15, taken along line G-G of FIG. 15, and with the adapter inserted into the catheter body.

FIGS. 16 and 17 depict cross sectional views of the catheter 1400, taken along lines F-F and G-G of FIG. 15, respectively. The cross-sectional view of the catheter 1400 shown in FIG. 16 generally shows a stair-step configuration, as previously discussed with respect to FIG. 8. On the distal side of the catheter 1400, this configuration is formed by the outer jacket segment 404, the outer tube 602, and the inner tube 604. On the proximal end, the configuration is formed by the first outer jacket segment 406, first inner layer 608, and second inner layer 610.

As with traces 102, wires 1402 may be embedded within a nonconductive portion of the catheter 1400 or may be formed on a surface (inner or outer) of any catheter layer. Similarly, and as shown in FIG. 16, multiple layers of longitudinally parallel and laterally aligned wires 1402a, 1402b may be employed in a single catheter and shielded from one another by intervening nonconductive material. Further, multiple wires may longitudinally overlap one another to create a continuous electrical path. For example, one wire 1402a may run between (or be co-extruded with, or sit in a depression formed on either) the second outer jacket segment 404 and outer tube 602. A second wire 1402c may sit between the first outer jacket segment 406 and first inner layer 608. These wires 1402a, 1402c generally at least partially overlap one another to form an electrical path running the length of the catheter 1400. The same may be true for wire segments 1402b, 1402d running between the outer tube and inner tube and outer jacket and inner layer, respectively.

FIG. 17 depicts a cross-sectional view of the mating junction between the catheter 1400 and adapter 900. Conceptually, this view is similar to the one shown in FIG. 9, except that wires 1402c, 1402d have been substituted for traces 102c, 102d. These wires 1402c, 1402d mate with adapter traces 122a, 122b to continue the aforementioned electrical path.

5. Lead Incorporating Embedded or Formed Traces or Wires

Any of the catheter embodiments described above may also function as a device lead having integrated traces 102 or wires 1402 and externally formed electrodes 104. One exemplary function for such a lead is to regulate tissue contraction (for example, the beating of a human heart) by providing regularly timed electrical impulses.

Generally, an embodiment of the present invention taking the form of a lead has a solid inner core 200 or tube, insofar as few if any medical devices must pass through the lead itself. Alternative embodiments, however, may include a lumen 116 running the length of the lead. If such a lumen 116 is present, it is generally closed at the distal end of the lead. For example, a closed-end lumen 116 may permit a stylette to run substantially the length of the lead, thus providing additional strength and rigidity to the lead. Typically affixed to the lead is a pacemaker or other power source capable of providing electrical impulses at timed intervals. The lead may also incorporate a diagnostic electrode 108 at or near the tip 106, in order to monitor the bioelectric impulses generated by the regulated tissue. In this manner, the lead may incorporate both the energy delivery or tissue regulating and diagnostic functions described herein. If a diagnostic function is provided, a discrete trace 102 generally operably connects each diagnostic electrode 104 (whether located along the shaft 110 or at the tip 106) to a diagnostic apparatus.

Although such electrical impulses may be delivered through any sufficiently conductive portion of the lead surface operably connected to a power source (such as a pacemaker), many leads are equipped with a tip or distal electrode 108. The location of the distal electrode 108 at the end of the lead provides a simplified contact point for ensuring that the electrode is in contact with the tissue, insofar as a doctor or surgeon must maneuver only the tip of the lead into contact. In alternative embodiments, the tip electrode 108 may be omitted and an electrode 104 located along the lead sheath 110 may be used to deliver electrical impulses. The lead may be permanently implanted, or may be intended for temporary use by a patient. An adapter 900, 1100, such as those described with respect to FIGS. 10 and 11, may also be provided to facilitate connection between the tip electrode 108 and the power source and/or the diagnostic electrode 104 and the diagnostic apparatus.

6. Method of Manufacture

With respect to one embodiment of the present invention (for example, the embodiment shown in FIGS. 1-5), different portions of a catheter or lead (collectively, "device" 100) are separately manufactured, then bonded together. Broadly, four separate portions are manufactured and bonded. In order from the distal to proximal ends of the device, these are: the tip 106, the portion of the device shaft 110 extending from the tip to a braided portion of the shaft, (the "distal shaft section"), the portion of the shaft 110 having a braided wire or fiber 118 (the "braided shaft section"), and the adapter 900, 1100. It should be noted that alternative embodiments may omit one or more of these sections. For example, an alternative embodiment may omit the braided shaft section, instead connecting the distal shaft section directly to the adapter 900, 1100. Yet another alternative embodiment may omit the distal shaft section, and instead bond the tip 106 directly to the braided shaft section.

Figure 18A:
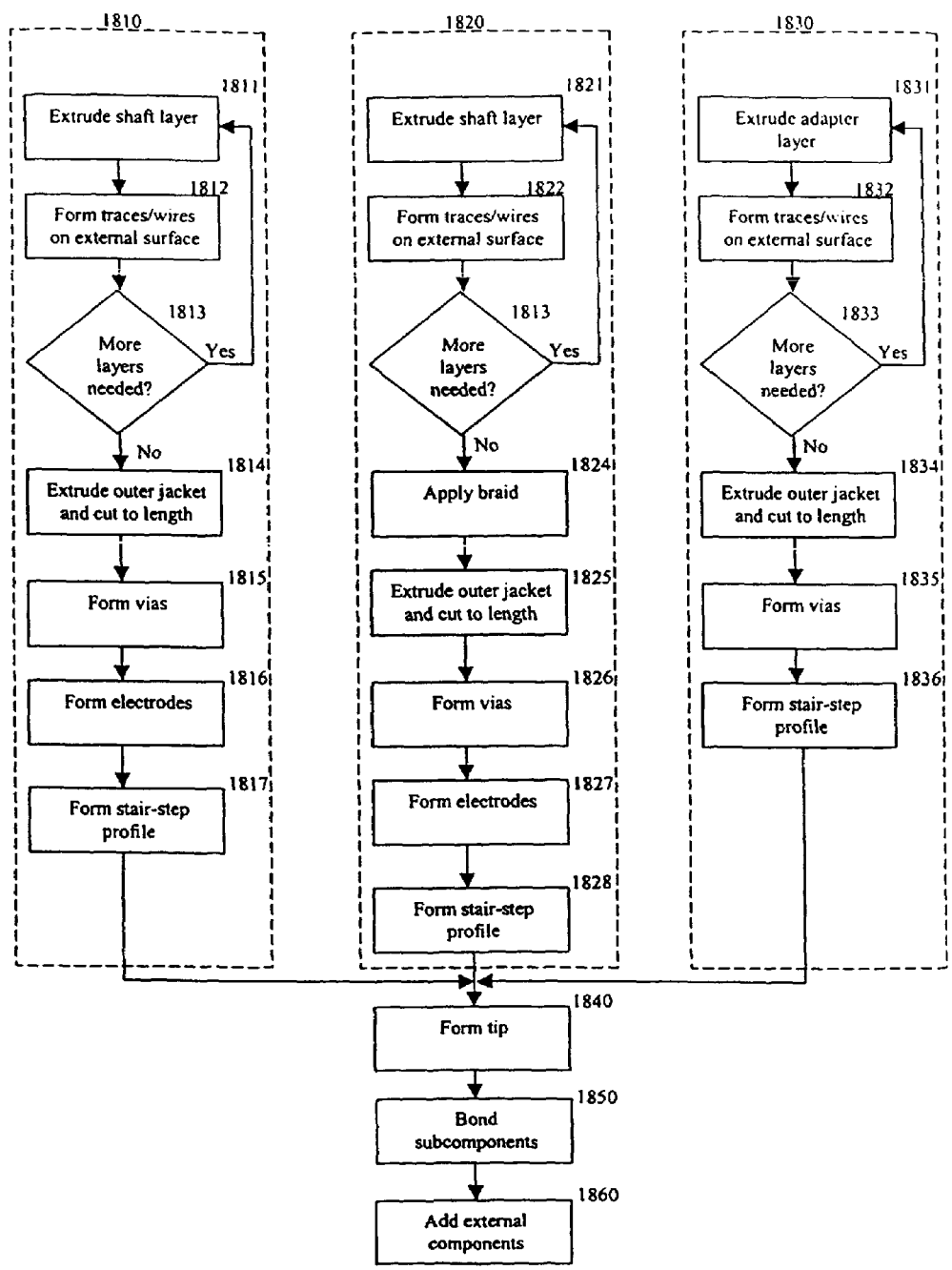
FIG. 18a is a flowchart depicting an exemplary method of manufacturing an embodiment of the present invention.

FIG. 18a is a flowchart depicting a first method for manufacturing a shaft 110 and adapter 900, 1100 of a medical device 100 having integrated traces 102, wires 1402, and/or electrodes 104. Generally, the manufacturing process consists of three main sub-processes 1810, 1820, 1830, each of which detail the manufacture of a specific catheter or lead component. These sub-processes may be performed in any order. For example, sub-process 1820, detailing the manufacture of a braided shaft section, may be performed before or after sub-process 1810, which depicts the manufacture of the distal shaft section.

Sub-process 1810 generally describes one exemplary method for manufacturing the distal shaft section. For example, in the embodiment shown in FIG. 8, sub-process 1810 details the manufacture of the inner tube 604, outer tube 602, and outer jacket 114 of the shaft 110, all extending between the tip 106 (not shown) and the braided portion 118 of the catheter. In other words, sub-process 1810 details the manufacture of those portions of the catheter shown in FIG. 6 to the left of the stair-step configuration, with the exception of the device tip 106.

First, in operation 1811, a layer of the shaft 110 is extruded. Generally, the innermost layer is extruded first. For example, in the embodiment shown in FIG. 6, the inner tube 604 may be extruded in operation 1811. Typically, the various concentric layers of the catheter 110 (i.e., tubes 112 and/or jacket 114s) are extruded from a nonconductive polymer material. The geometry of each layer is dictated by the catheter shape, size, and function.

Next, in operation 1812, traces 102 and/or wires 1402 are placed on the external surface of the layer, as necessary. It should be noted that operation 1812 is entirely optional; a layer may include no conductive traces 102 or wires 1402. As part of this operation, traces are formed in or on the layers, presuming the traces and/or wires are not co-extruded. The conductive traces 102 may be placed on a single layer or spread across multiple layers of nonconductive substrate. In either case, conductive material may be electro-deposited or sputtered on the nonconductive member, or built up and adhered by any other conventionally known means.

Another manner of creating the conductive traces 102 is to create grooves or depressions 126 in the nonconductive material forming a tube 112 or jacket 114 and selectively deposit conductive material into the grooves. These grooves 126 may be formed during the extrusion process, or may be carved out of the tube or jacket surface as a separate operation. Either electro-deposition or sputtering may be used to place conductive material within the groove.

In yet another example, conductive material may be uniformly placed around a cylindrical substrate having grooves or depressions 126 where traces 102 are desired. Once the conductive material is placed, all such material projecting above the surface of the nonconductive substrate may be removed through abrasion, leaving only the desired traces 102 flush with the layer surface. Typically, this creates a trace 102 on the outer surface of the substrate.

Alternatively, instead of forming traces 102 though a deposition process, traces may be formed by uniformly coating the cylindrical surface and then selectively removing conductive material from undesired locations either by application of chemicals or by vaporizing the conductive material with laser light. Multiple trace 102 layers may be built up by alternating extrusion of additional nonconductive substrate over a conductive layer with extrusion of a conductive layer. Generally, however, the outermost jacket 114 of the catheter is made of a nonconductive material.

If conductive traces 102 are not capable of carrying electrical energy in sufficient quantities to permit the catheter to operate as desired, fine gauge wire 1402 may be incorporated into the nonconductive substrate during the extrusion process. The wires may be attached to the mandrel and fed off a spool under tension. The position of the wires 1402 with respect to the mandrel may be maintained by the tension on the wires, the wire path at the extrusion die, and position of the extruded material. Alternatively, wires 1402 may be placed within the aforementioned grooves or depressions or placed between concentric layers instead of being extruded with the substrate comprising each layer.

Regardless of the method by which the traces 102 or wires 1402 are formed or extruded, these electrically conductive elements are generally integrally formed with the catheter. That is, once formed, the trace or wire generally is not removable, but instead is relatively permanently affixed within the catheter body.

Following operation 1812, in operation 1813 it is determined whether additional concentric inner layers of the distal shaft section will be formed. A distal shaft section may have multiple concentric layers. Continuing the reference to the embodiment of FIG. 6, the outer tube 602 surrounds the inner tube 604, constitutes a separate "inner layer" for purposes of this determination, and is extruded over the inner tube. Generally, an "inner layer" of the shaft refers to any layer of the catheter or lead shaft except the outer jacket 114. If additional layers need be extruded over existing layers, then operation 1811 is again performed, and the next concentric layer is extruded. After operation 1811, traces and/or wires are formed on the next concentric inner layer, if required. Typically, the process of extruding a concentric inner layer over a previously-extruded inner layer also bonds the layers together.

If, however, additional layers are not required (either because only a single layer is necessary or all layers have been extruded), the outer jacket 114 is extruded in operation 1814. Once the outer jacket is extruded, the distal shaft section is cut to the desired length. Generally, the outer jacket 114 is formed of the same nonconductive polymer as the inner layers, and is extruded over the inner layers. However, alternative embodiments may manufacture the outer jacket 114 from a different substance, such as a second nonconductive polymer. Further, the outer jacket may incorporate co-extruded traces 102 or wires 1402, or such wires/traces may be formed on the outer jacket in any of the manners described with respect to operation 1812.

In operation 1815, vias are formed through the distal shaft section. The formation of vias at least partially exposes the traces 102 or wires 1402, and provides a pathway to electrically connect the traces or wires to an electrode 104. Typically, the location of the via is chosen to underlie the eventual location of an electrode. The via generally takes the form of a hole extending from the outer surface of the catheter 100 to the conductive trace 102 buried within the catheter. A conductive filament may be placed in the via to connect the electrode 104 to the trace, or the trace may extend or be built up through the via. Once the via is in place above the trace 102, the remainder of the via may be filled with conductive material to seal open portions. It should be noted that this operation may be skipped entirely, insofar as the distal shaft section may not include any electrodes 104.

In operation 1816, electrodes 104 are formed on the outer jacket 114 of the distal shaft section. As with the previous operation, this operation may be omitted if electrodes are formed only on the device tip 106 and not along any portion of the shaft 110. Generally, electrodes may be formed of a single or multiple types of metal, or any other suitable electrically conductive element. If multiple metals are used, the inner metal of an electrode 104 is typically selected for its adhesion to the nonconductive substrate and the outer metal layer is selected for biocompatibility. Exemplary biocompatible materials include gold and platinum. Intermediate metals, if any, may be selected for appropriate cohesive and electrical properties. The electrode metals, taken together, form an integrated electrode capable of faithfully transmitting bio-electric current from target tissue to a diagnostic device attached to the catheter, or electrical energy from such a device to the electrode. Electrodes 104 may be formed by sputtering, electro-deposition, depositing of metal into a depression on the catheter surface, and so forth. As with traces 102, depressions 126 may be formed on the catheter surface to assist in placing and creating an electrode.

As with the traces 102, above, the electrodes 104 or other energy delivery elements are typically integrally formed with the catheter body, and are generally not removable therefrom.

Next, in operation 1817, the "stair-case" profile discussed in more detail above is formed. Generally, this profile is formed by cutting, planing, grinding, or otherwise removing material from inner or outer layers. More material is progressively removed from each layer.

Generally, the proximal end of any given portion of the catheter 100 (distal shaft section, braided shaft section, adapter etc.) is configured so that the innermost layer extends beyond the outermost layer, while the distal end of any given portion is configured in reverse. In other words, portions of the outer jacket 114 and outer tube 602 (if any) are removed at the proximal end of the distal shaft section, so that the innermost layer (in the example of FIG. 6, the inner tube 604) extends furthest at the proximal end. Conversely, the inner nonconductive tubes and/or inner layers of the distal end of distal shaft section may be cored in a stair-step configuration to exposing the traces. In this manner, the proximal end of one section (for example, the distal shaft section) fits within the distal end of an adjacent section (for example, the braided shaft section). This transition is shown generally in FIG. 6. Alternative embodiments may reverse the stair-step configuration of the distal and proximal ends of any given section. Any required internal components (for example, portions of a steering mechanism, a stylette, a lead, and so forth) may also be added in this operation.

Sub-process 1820 generally describes the manufacture of the braided shaft section. For reference, the "braided shaft section" refers to a portion of the catheter or lead shaft 110 incorporating a braided material 118, as discussed in more detail above. Generally, the method of manufacturing the braided shaft section is similar to the method of manufacturing the distal shaft section.

In operation 1821, a shaft layer of the braided shaft section is extruded. The first time this operation is executed, the extruded layer is the innermost tube 112 or lumen 116. As with operation 1811 of sub-process 1810, the various concentric layers of the catheter (i.e., tubes 112 and/or jackets 114) are extruded from a nonconductive material. The geometry of each layer is dictated by the catheter shape, size, and function. In an alternative embodiment, the braided material 118 may be co-extruded with any shaft layer, as desired.

In operation 1822, traces 102 are formed on the surface of the layer extruded in 1821. Generally, this operation is performed in a manner similar to that of operation 1812. Any or all of the methods described with respect to operation 1811 or elsewhere herein for forming traces 102 or wires 1402 (or co-extruding traces or wires) may be used in this operation.

Next, in operation 1823, it is determined whether additional inner layers must be extruded. Again, an "inner layer" in this context refers to any layer of the braided shaft section except the outer jacket 114. If additional inner layers are required or desired, then operation 1821 is again executed and the next concentric inner layer is extruded over the most recently extruded inner layer.

If no additional inner layers are to be formed, then in operation 1824 the braid 118 is applied. As previously mentioned, the braid 118 may be made of a metal or nonconductive fiber. The braid is typically applied to the braided shaft section and sits between the outermost "inner layer" and the outer jacket 114. In alternative embodiments, the braid 118 may be placed between two inner layers, multiple braids may be used, or the braid may be co-extruded with any inner layer or the outer jacket 114. Further, in alternative embodiments, the braid may be placed between inner layers, instead of between the outermost "inner layer" and the outer jacket. In an alternative embodiment employing co-extruded braided material 118, this operation is typically omitted.

Typically, the braid material 118 is chosen according to the torque characteristics and column strength desired for the finished catheter. The braid material may also be chosen to minimize electrical signal interference, or "noise," caused in the traces 102 or wires 1402 by external electrical signals generated, for example, by tissue. The braid material 118 may be incorporated into any layer of the catheter during extrusion, or may be added between or atop a tube 112 or jacket 114 prior to final assembly. In one embodiment, this material takes the form of braided, criss-crossing wires.

Next, in operation 1825 the outer jacket 114 is extruded and cut to length. This operation is similar to the process described with respect to operation 1814.

In operation 1826, vias are formed through the outer jacket 114 and any inner layers, if necessary. Because the braided shaft section is located closer to the proximal end of the catheter or lead when assembled, it may not include electrodes 104 formed on its outer surface. In such a case, there is no need to form a via. If, however, one or more vias are formed, the process is generally the same as that described with respect to operation 1815.

In operation 1827, electrodes 104 may be formed on the exterior of the braided shaft section (i.e., on the outer sidewall of the outer jacket 114). Again, this operation may be omitted in some embodiments. When this operation is executed, it may be performed in any of the manners described above with respect to operation 1816 of the distal shaft section sub-process 1810. Any required internal components (for example, portions of a steering mechanism, a stylette, a lead, and so forth) may also be added in this operation.

Finally, the last operation of sub-process 1820 is executed. In operation 1828, the previously-discussed stair-step profile is formed in the manner generally set forth with respect to operation 1817.

In sub-process 1830, the adapter 900, 1100 is formed. Although two different types of adapter are disclosed herein, sub-process 1830 generally sets forth the method for manufacturing either adapter.

Initially, in operation 1831, a layer of the adapter 900, 1100 is extruded in the manner described above with respect to operation 1811. Next, in operation 1832, traces are formed on the external (or, if desired, internal) surface of the extruded layer. Adapter traces 122 (or wires, in some embodiments) are formed in the manner discussed above with respect to the formation of catheter traces 102.

In operation 1833, it is determined if additional adapter layers 500, 902, 904 are to be extruded. If so, then sub-process 1830 returns to operation 1831 and another adapter layer is extruded.

Otherwise, operation 1834 is executed. In operation 1834, the outer jacket 500 of the adapter 900, 1100 is extruded and cut to the appropriate length. After extruding the outer jacket 500, vias are formed in operation 1835. It should be noted that not all adapters 900, 1100 require vias. Accordingly, operation 1835 may be omitted when manufacturing some embodiments.

Finally, in operation 1836, the customary stair-step profile is created on the adapter 900, 1100. For example, this operation may form the plug portion 1000 of an adapter. The process for creating a stair-step profile is generally discussed with respect to operation 1817. Any required internal components (for example, portions of a steering mechanism) may also be added in this operation.

After sub-processes 1810, 1820, 1830 are complete, the catheter tip 106 is typically formed in operation 1840. Alternatively, the tip 106 may be formed during sub-process 1810. Generally, the tip may be formed by overmolding additional nonconductive material onto the end of the distal shaft section, by heat bonding the end of the distal shaft section closed, by adding additional nonconductive material to close any opening at the end of the distal shaft section, by mechanically- or pressure-sealing closed the end of the distal shaft section, and so forth.

As previously mentioned, the catheter may include a tip electrode 108. As part of operation 1840, the tip electrode may be formed by conventional means, or alternatively by plating a metal electrode over molded non-conductive tip shape. A conductive trace 102 may be connected to the metal electrode through a via. If a tip electrode is not required, the molded tip assembly may be formed without the metal electrode or conductive traces and bonded to the distal end of the catheter. In either case, the molded tip shape may contain radiopaque material to enhance visualization during fluoroscopy.

In operation 1850, the various components manufactured during the sub-processes 1810, 1820, 1830, as well as the device tip 106, are bonded to one another. In general, the male stair-step portion of one subcomponent is inserted into the female stair-step cavity of the adjacent subcomponent. Heat-, adhesive-, chemical-, pressure-, or sonic-bonding may all be used to bond a layer of one component to an adjacent, underlying or overlying layer of a second component.

For example and with reference to FIG. 8, the first outer jacket segment 406 partially overlies the outer tube 602. In operation 1850, the first outer jacket segment 406 may be bonded to the outer tube 602. Likewise, the first inner layer 608 may be bonded to the inner tube 604. This operation may also bond elements to longitudinally adjacent elements, although this is not required. Continuing the example, the end of the first inner layer 608 may also be bonded to the end of the outer tube 604 where the two abut.

Generally, since traces 102 in adjacent sections of the shaft 110 were exposed in steps 1817 and 1828, when properly aligned the traces may form a continuous electrical path. This process may be repeated if multiple tubes are nested within one another inside the catheter. Similarly, this is true of the connection between catheter traces 102 and adapter traces 122.

An alternative method for joining adjacent tubes 112 and/or jacket segments 404, 406, as well as corresponding conductive traces 102, is to heat bond the non-conductive tube portions, while simultaneously bonding the conductive traces with solder paste. The solder paste may be selected to flow within a temperature range required to bond the non-conductive layers. Optionally, a ring of non-conductive material (such as that used to form the tube 112 or jacket 114) may be placed between adjacent tubes to ensure electrical isolation of different conductive traces 102 or wires 1402.

Finally, in operation 1860, any external components may be added. For example, a handle to operate a steering mechanism may be added in this operation, or a pacemaker attached to a lead running the length of the catheter 100.

Although the above process 1800 and sub-processes 1810, 1820, 1830 have been described with particular operations set forth in a particular order, several operations may be omitted or performed out of order. For example, a stair-case profile may be formed for the distal shaft section in operation 1817 prior to forming electrodes in operation 1816 or via in operation 1815. This is but a single example; other operations may also be rearranged without deviating from or impacting the method of manufacture set forth herein.

Although the above operations are listed in a given order, it should be understood that an embodiment of the present invention may be manufactured by a method omitting some operations, adding others, and/or changing the order in which operations are executed. For example, electrodes may be formed prior to or simultaneously with traces. Accordingly, the aforementioned operations are illustrative of the manner of manufacture of a single embodiment of the present invention, and should not be construed as limiting all embodiments or all possible methods of manufacture.

Figure 18B:
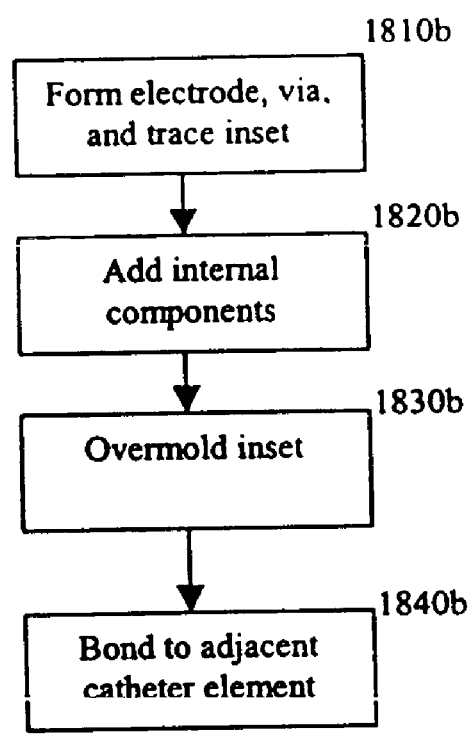
FIG. 18b is a flowchart depicting an exemplary method of overmolding a catheter or lead shaft containing embedded traces or wires.

FIG. 18*b* depicts a method for extruding a shaft. First, in operation 1810*b*, an electrode 104, via, and trace 102 (or wire 1402) are formed and linked to one another to provide an energy delivery or sensing structure. Unlike the method of manufacture described above with respect to FIG. 18*a*, in this method the energy delivery structure is formed in a skeletal state.

Next, in operation 1820*b*, any internal components (i.e. stylette, instrument lead and so forth) are suspended in place beneath or within the skeletal energy delivery structure. In other words, the internal components are placed relative to the energy delivery structure so that they will occupy the lumen 116 or center of the solid core 200 when the shaft 110 is formed.

In operation 1830*b*, the shaft 110 is overmolded over the skeletal energy delivery structure and/or internal components. As part of this operation, the distal and proximal ends of the shaft section may be overmolded to provide the stair-step configuration previously discussed. Finally, in step 1840*c*, the shaft 110 is bonded to the adjacent catheter 110 elements, generally the tip 106 and adapter 900, 1100. If necessary, portions of the overmolded shaft 110 may be removed to expose the electrode 104 or trace 102.

The aforementioned overmold process may generally be used to form an adapter as well. This process is generally the same as that described with respect to FIG. 18*b*.

7. Arbitrarily Shaped Electrodes

Figure 19:
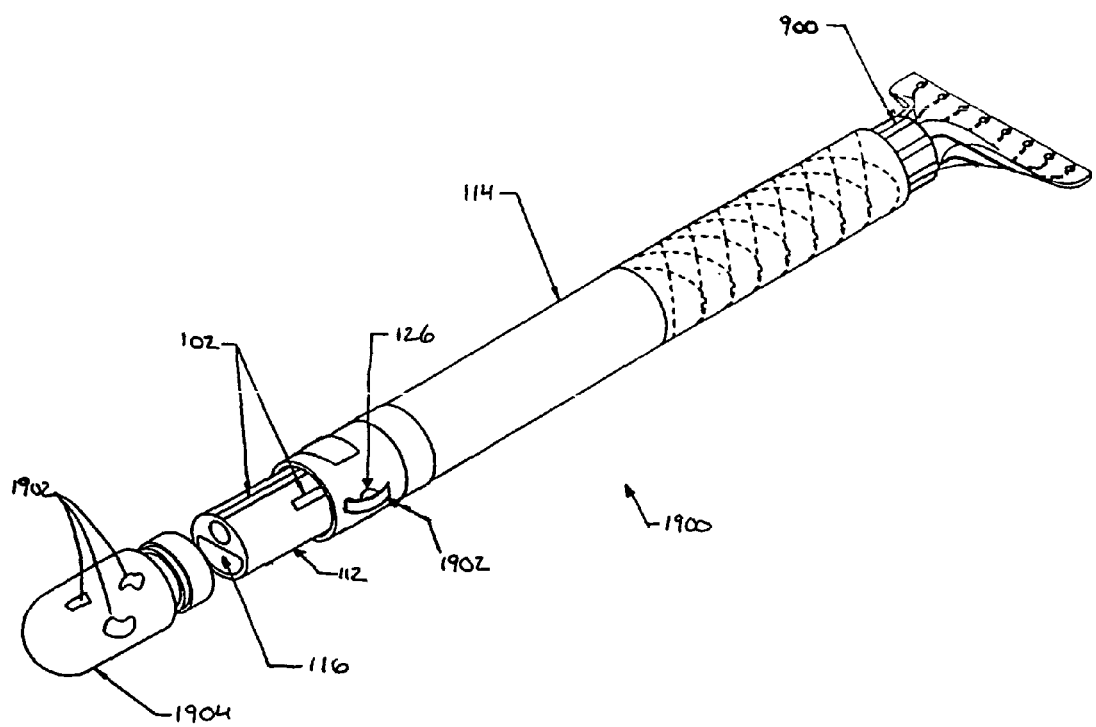
FIG. 19 depicts an isometric, partially-exploded view of a catheter having arbitrarily shaped electrodes.

FIG. 19 depicts a partially-exploded view of a catheter 1900 having arbitrarily shaped electrodes 1902. In the present embodiment, several arbitrarily-shaped electrodes are located on the catheter's 1900 tip portion 1904, and one along the sidewall of the catheter jacket 114. The term "arbitrarily shaped," as used herein, refers to the fact that the electrodes 1902 may be manufactured in any size and shape desired, and should not be taken to imply that the shape and/or size of the electrodes 1902 are random. Arbitrarily shaped electrodes as described herein may be located at any point along the exterior sidewall of the catheter jacket 114 of tip 1904.

Generally, the arbitrarily shaped electrodes 1902 may be used for either energy delivery (i.e., ablation) or diagnostic purposes (i.e., mapping). As with prior embodiments, the electrodes 1902 are often mounted on the sidewall of the catheter jacket 114, which in turn is constructed of nonconductive material. Arbitrarily-shaped electrodes 1902 may also be formed on the catheter tip 1904, as shown in FIG. 19. Conductors, such as the embedded or formed traces 102 or wires 1402 (not shown) previously discussed, may conduct electricity between the electrode 1902 and a medical device attached to the catheter's proximal end. Such connection may, for example, be facilitated by the adapters 900, 1100 of FIGS. 10 and 11. A temperature monitor, such as the thermistor 124 and/or thermocouple discussed above, may also be affixed to the tip 1904. Neither a thermistor 124 nor thermocouple are depicted on FIG. 19.

In order to insulate the electrodes 1902 from one another and from adjacent, non-corresponding traces 102, the tip 1904 assembly may be overmolded. Further, overmolding the tip 1904 assembly with respect to the electrodes 1902 and/or conductive elements 102, 1402 provides support to both the electrodes 1902 and conductive elements, minimizing the possibility of damaging or breaking these elements. The overmolding also provides a generally smooth finish for the tip 1904, thus minimizing the possibility of inadvertently damaging tissue due to tip discontinuities.

In a first exemplary method for manufacturing the arbitrarily shaped electrodes 1902, the electrodes may be shaped as desired from any sufficiently conductive, biocompatible material, such as platinum or gold. Fine wires 1402 (not shown) may be soldered to the base of each electrode 1902, and the electrode and wire assembly may be mounted on or in a solid, flexible nonconductive tube 112, such as any layer forming part of the catheter 1900. Generally, the wires 1402 and electrodes 1902 are fixed along such a tube 112 in positions corresponding to the final placement of the electrodes on the tip 1904 or catheter 1900 sidewall. The tube 112 (with mounted wires) may be overmolded with a nonconductive material. This overmolding generally forms the tip 1904 and/or jacket 114. Excess material may be removed through cutting or abrasion to shape the tip 1904 and expose the electrodes 1902. Presuming the overmolding does not form a catheter jacket 114, the tube may then be placed within such a jacket and bonded thereto.

In a second method for constructing the arbitrarily-shaped electrodes 1902, the electrodes may be electro-deposited or sputtered into arbitrarily-shaped holes or depressions 126 on the exterior of the jacket 114 or tip 1904. (It should be noted that the depression 126 shown on FIG. 19 is somewhat exaggerated for clarity. In many embodiments, the depression 126 may be completely or nearly completely filled by the electrode 1902, thus hiding the depression from sight.) Generally, this sputtering or depositing may completely fill the depression 126, or may leave a portion of the depression empty to allow later passage of a wire or via through the empty section in order to connect the electrode 1902 to a trace 102, wire 1402, or other conductive element. Alternatively, the depression 126 may extend completely through the tip 1904 or jacket 114, and the electrode 1902 may similarly extend throughout the entirety of the tip 1904 or jacket 114. Since such an electrode 1902 extends from the exterior to the interior of the catheter 1900, a via may not be required.

Alternatively, wires 1402 may be run along the exterior of a tube 112, or within the lumen 116 of a tube. The tube 112 may then be overmolded as previously described and affixed to a jacket 114, thus providing the finished catheter 1900 with a through lumen 116.

If necessary, a portion of the jacket 114 may similarly be removed to expose the trace 102. This may be required, for example, where the arbitrarily-shaped electrode 1902 is formed on the exterior jacket 114 surface, while the trace 102 is formed on or in the tube 112 or jacket interior. The trace 102 may then be electrically connected to the arbitrarily-shaped electrode 1902.

Similarly, conductive traces 112 may be electro-deposited or sputtered on the exterior of the jacket 114, or wire 1402 may be extruded through the jacket 114 or tube 112 sidewalls. Vias may be formed by removing portions of nonconductive sheath material sufficient to expose traces 102 or wires 1402 and inserting a connector (such as a fine conductive wire) into the hole formed by removal. The via may then connect the aforementioned trace 102 or wire 1402 to an electrode 1902 of arbitrary shape and size.

Once an electric connection is established between the trace 102 and the electrode 1902, the assembly may be overmolded as discussed above, and material may be cut or abraded away to expose the electrodes 1902. As also previously mentioned, multiple tubes 112 may abut end-to-end in order to form a continuous catheter 1900 body. In such a case, the distal end of each trace 102 may be exposed by removing nonconductive material from either an upper or lower surface of the trace, permitting adjacent traces to mate as necessary. This process was more fully discussed with respect to FIG. 18. Nonconductive material may similarly be removed expose a sufficient portion of the trace 102 in order to permit mating with an electrode 1902, an adapter 900, or directly to a medical device.

As with previously discussed embodiments, various steering mechanisms may be employed with the present embodiment. For example, a wire guide assembly may be connected to the distal end of the catheter 1900, or a fluid guide assembly may also be so connected.

8. CONCLUSION

As will be recognized by those skilled in the art from the foregoing description of embodiments of the invention, numerous variations on the described embodiments may be made without departing from the spirit and scope of the invention. For example, the exact number of layers used to form a catheter may vary from embodiment to embodiment, as may the material and composition of the catheter. Further, while the present invention has been described in the context of specific embodiments and methods of manufacture, such descriptions are by way of example and not limitation. Accordingly, the proper scope of the present invention is specified by the following claims and not by the preceding examples.

What is claimed is:

1. A method of manufacturing a medical device comprising:
    forming a device body by extruding a first cylindrical body layer;
    extruding a second cylindrical body layer;
    placing the second body layer within the first body layer; and
    bonding the second body layer to the first body layer;
    forming a first electrically conductive element on the device body;
    forming a first electrode on the device body; and
    operably connecting the first electrode and the first electrically conductive element.

2. The method of claim 1, wherein the step of forming a first electrically conductive element on the device body comprises co-extruding a first electrically conductive element within the device body.

3. The method of claim 1, wherein the step of forming a first electrically conductive element on the device body comprises electro-depositing a conductive material on a nonconductive portion of the device body.

4. The method of claim 1, wherein the step of extruding the second cylindrical body layer comprises extruding the second cylindrical body layer over the first cylindrical body layer.

5. The method of claim 1, wherein the step of forming a first electrode on the device body comprises the steps of:
    forming a groove on at least a portion of the device body;
    depositing conductive material within the groove in a shape of the first electrode; and
    in the event that a portion of the conductive material extends beyond an upper surface of the groove, removing the portion of conductive material.

6. The method of claim 5, wherein the step of forming a groove on at least a portion of the device body is performed simultaneously with the step of forming the device body.

7. The method of claim 1, wherein the step of forming a first electrically conductive element on the device body comprises the steps of:
    co-extruding electrically conductive material with the first cylindrical body layer; and
    removing a portion of the first cylindrical body layer to expose at least a portion of the electrically conductive material.

8. The method of claim 1, wherein the step of forming a first electrically conductive element on the device body comprises:
    coating a surface of the device body with an electrically conductive material; and
    selectively removing at least a portion of the electrically conductive material from the device body.

9. The method of claim 8, wherein the step of selectively removing at least a portion of the electrically conductive material from the device body comprises exposing at least a portion of the electrically conductive material to a chemical solvent.

10. The method of claim 8, wherein the step of selectively removing at least a portion of the electrically conductive material from the device body comprises vaporizing at least a portion of the electrically conductive material with a laser.

11. The method of claim 1, wherein the step of forming a first electrically conductive element on the device body comprises extruding a conductive layer across at least a portion of the device body.

12. The method claim 11, further comprising:
  extruding a second device body longitudinally encasing the device body and extruded conductive layer; and
  extruding a second conductive layer across at least a portion of the second device body.

13. The method of claim 12, further comprising the steps of:
  forming a tip structure; and
  affixing the tip structure to the device body.

14. The method of claim 13, wherein the step of forming a tip structure comprises:
  plating a metal electrode over a molded non-conductive tip shape;
  forming a via in the tip shape; and
  electrically connecting a trace to the metal electrode through the via.

15. The method of claim 1, wherein the step of forming a first electrically conductive element on the device body comprises:
  feeding wire from a spool to a mandrel under tension;
  positioning the wire with respect to an ultimate location along the device body means of the mandrel; and
  co-extruding the wire with the device body.

16. The method of claim 1, wherein the step of forming a first electrically conductive element on the device body comprises:
  forming a groove on an exterior surface of the device body; and
  placing a wire within the groove.

17. The method of claim 1, further comprising the step of affixing an adaptor to a distal end of the device body.

18. The method of claim 17, wherein the step of affixing an adapter to a distal end of the device body comprises:
  aligning an adapter trace with the first electrically conductive element with an adapter trace; and
  inserting a portion of the adapter into the distal end of the device body such that the adapter trace and electrically conductive element are operably connected.

* * * * *